United States Patent
Pudney

(10) Patent No.: US 10,900,903 B2
(45) Date of Patent: Jan. 26, 2021

(54) PROTEIN STRUCTURE ANALYSIS BASED ON RED-EDGE EXCITATION SHIFT (REES) SPECTROSCOPY

(71) Applicant: UNIVERSITY OF BATH, Bath (GB)

(72) Inventor: Christopher Roland Pudney, Bath (GB)

(73) Assignee: UNIVERSITY OF BATH, Bath (GB)

(*) Notice: Subject to any disclaimer, the term of this patent is extended or adjusted under 35 U.S.C. 154(b) by 327 days.

(21) Appl. No.: 16/085,968

(22) PCT Filed: Mar. 17, 2017

(86) PCT No.: PCT/GB2017/050743
§ 371 (c)(1),
(2) Date: Sep. 17, 2018

(87) PCT Pub. No.: WO2017/158371
PCT Pub. Date: Sep. 21, 2017

(65) Prior Publication Data
US 2019/0072491 A1 Mar. 7, 2019

(30) Foreign Application Priority Data

Mar. 18, 2016 (GB) .................................. 1604640.1

(51) Int. Cl.
*G01N 1/00* (2006.01)
*G01N 21/64* (2006.01)
*G16C 20/30* (2019.01)
*G16C 20/40* (2019.01)

(52) U.S. Cl.
CPC ......... *G01N 21/6486* (2013.01); *G01N 21/64* (2013.01); *G16C 20/30* (2019.02);
(Continued)

(58) Field of Classification Search
None
See application file for complete search history.

(56) References Cited

U.S. PATENT DOCUMENTS

2010/0086951 A1* 4/2010 Hedley ............. G01N 33/5041
435/7.24
2013/0137127 A1 5/2013 Berezin et al.
2014/0099724 A1 4/2014 Skach et al.

FOREIGN PATENT DOCUMENTS

WO WO 2014/138919 A1 9/2014

OTHER PUBLICATIONS

Chaudhuri A et al.: "Organization and dynamics of tryptophans in the molten globule state of bovine alpha-lactalbumin utilizing wavelength-selective fluorescence approach: Comparisons with native and denatured states," Biochemical and Biophysical Research Communications, Elsevier, Amersterdam, NL, vol. 394, No. 4, Mar. 24, 2010, pp. 1082-1086, XP027009695, ISSN: 0006-291X, DOI: 10.1016/J.BBRC.2010.03.130.
(Continued)

*Primary Examiner* — Jyoti Nagpaul
(74) *Attorney, Agent, or Firm* — Keller Jolley Preece

(57) ABSTRACT

A protein structure analysis method includes receiving a fluorescence emission spectrum generated by a protein sample at a first excitation wavelength, evaluating, from the fluorescence emission spectrum, an indication characteristic of a fluorescence response of the protein sample at the first excitation wavelength, and repeating the receiving and evaluating steps in relation to a plurality of fluorescence emission spectra generated by the protein sample at a different excitation wavelength to the first excitation wavelength. In addition, the method includes generating a non-linear relationship between excitation wavelength and indication characteristic of fluorescence response of the protein sample that includes an indication of at least one characteristic of the conformational state of the protein sample. The method can be used with any protein which includes one or more naturally occurring fluorescent amino acids (intrinsic (Continued)

fluorophores), and particularly those with Trp residues (most), or proteins having appropriately selected extrinsic fluorophores.

19 Claims, 12 Drawing Sheets

(52) U.S. Cl.
CPC ..... *G16C 20/40* (2019.02); *G01N 2021/6419* (2013.01); *G01N 2021/6421* (2013.01); *G01N 2021/6439* (2013.01)

(56) References Cited

OTHER PUBLICATIONS

Klajnert B et al.: "Interactions between PAMAM dendrimers and bovine serum albumin," Biochimica et Biophysica ACTA (BBA)—Proteins & Proteomics, Elsevier, Netherlands, vol. 1648, No. 1-2, 2003, pp. 115-126, XP004425348, ISSN: 1570-9639, DOI: 10.1016/S1570-9639(03)00117-1.

H. Raghuraman and Chattopadhyay A: "Effect of ionic strength on folding and aggregation of the hemolytic peptide melittin in solution," Biopolymers, vol. 83, No. 2, May 5, 2006, pp. 111-121, XP055372897, US ISSN: 0006-3525, DOI: 10.1002/bip.20536.

Sourav Haldar et al.: "Monitoring Orientation and Dynamics of Membrane-Bound Melittin Utilizing Dansyl Fluorescence," The Journal of Physical Chemistry B, vol. 112, No. 44, Sep. 10, 2008, pp. 14075-14082, XP055191094, ISSN: 1520-6106, DOI: 10.1021/jp805299g.

Dragana A.M Catici et al.: "The red edge excitation shift phenomenon can be used to unmask protein structural ensembles: implications for NEMO-ubiquitin interactions," Febs Journal, vol. 283, No. 12, Jun. 9, 2016, pp. 2272-2284, XP055372304, GB ISSN: 1742-464X, DOI: 10.1111/febs.13724.

* cited by examiner

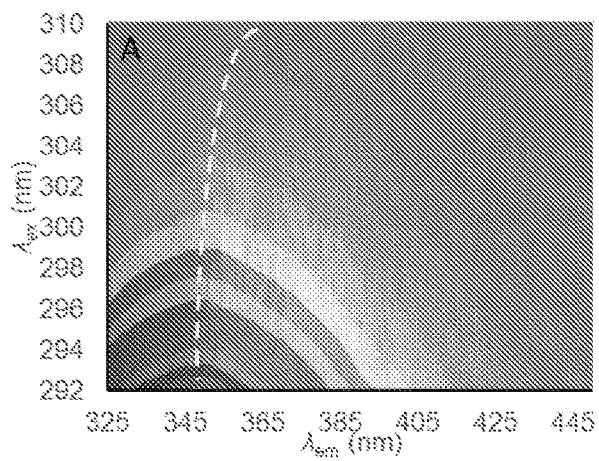 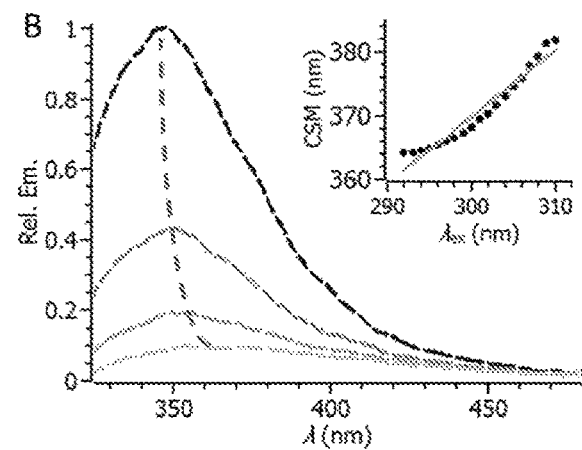
Figure 1a　　　　　　　　Figure 1b
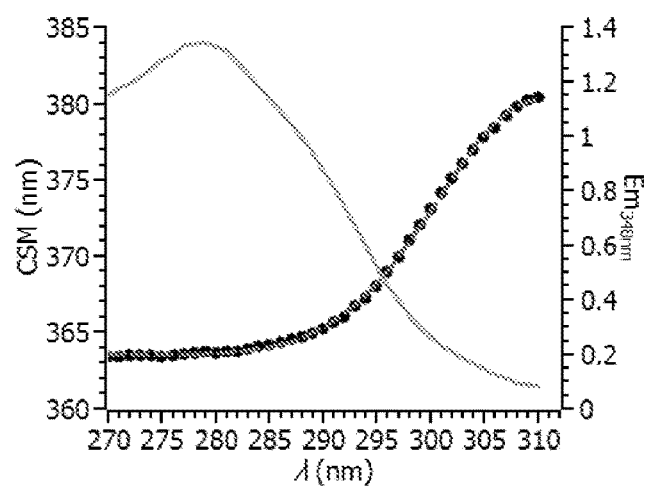
Figure 2

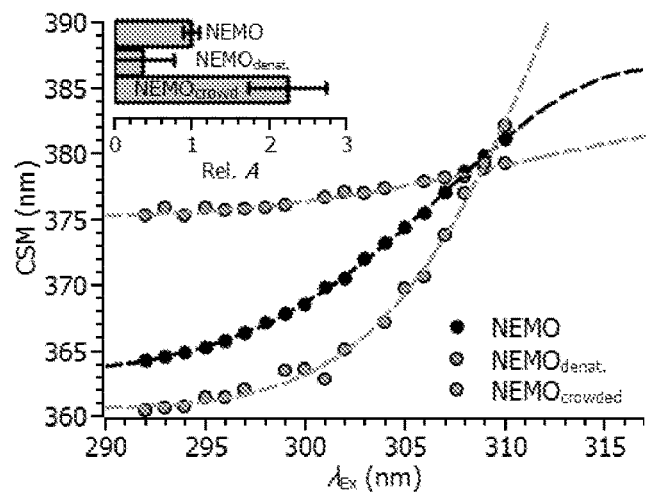
Figure 3
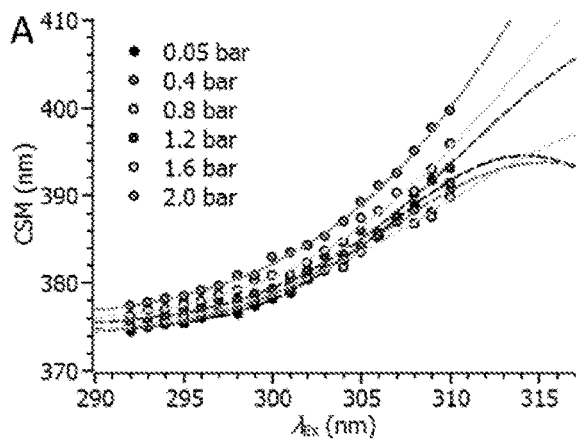 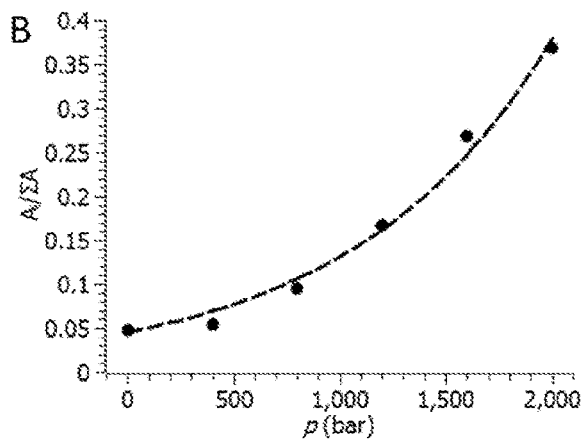
Figure 4a                                    Figure 4b

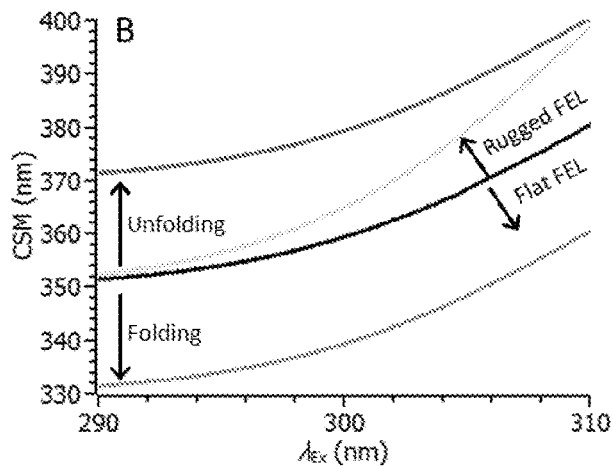
Figure 5
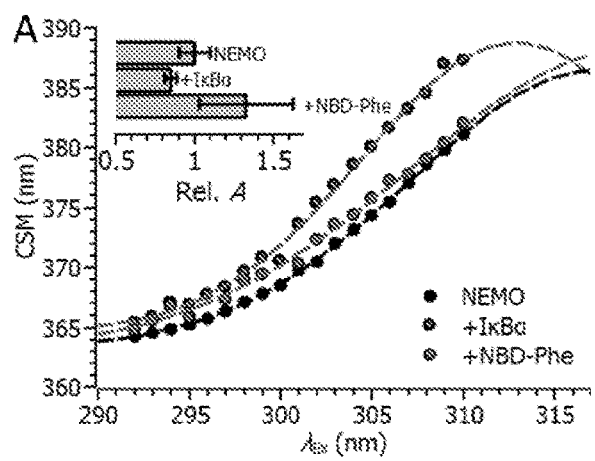 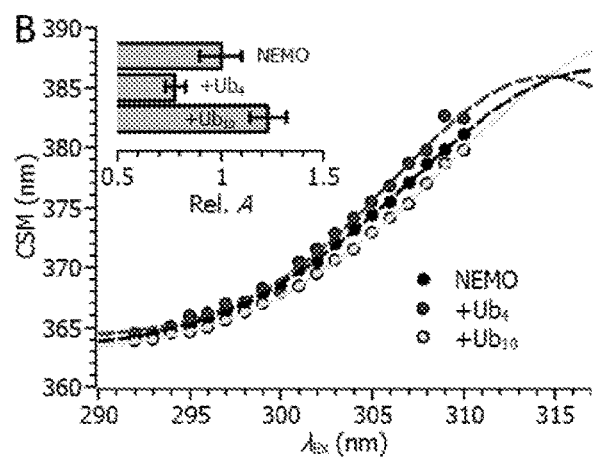
Figure 6a            Figure 6b

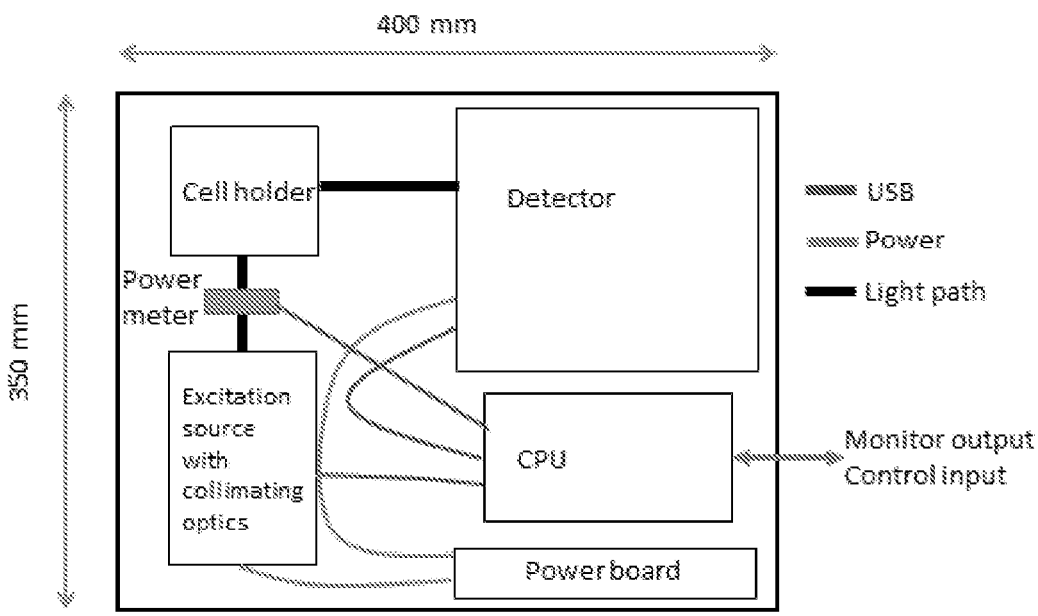
Figure 11
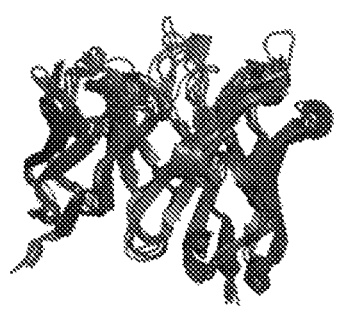
(a)
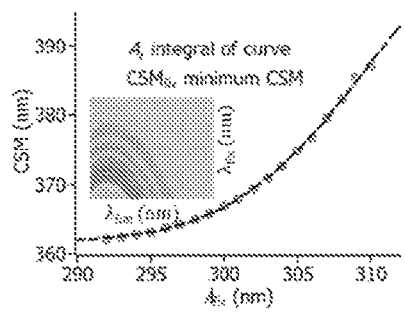
(b)
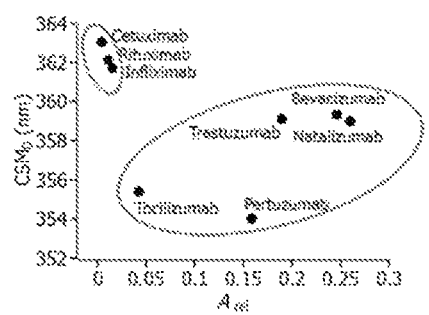
(c)
Figures 12a to 12c

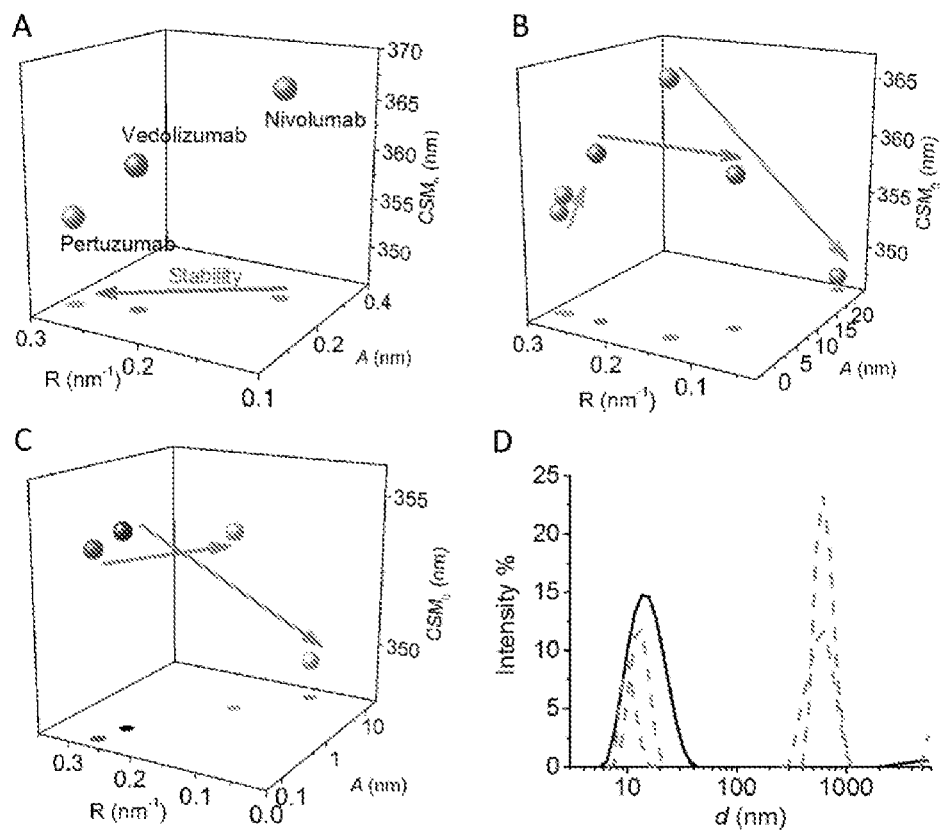
Figures 16A to D
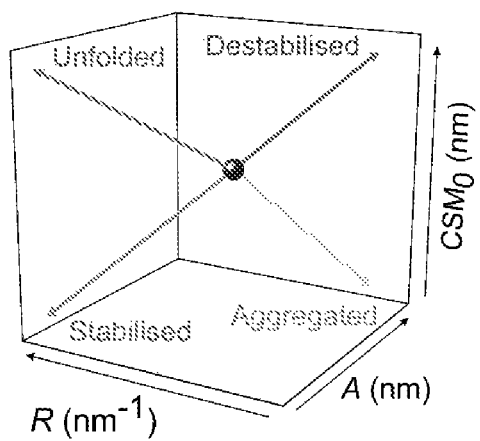
Figure 17

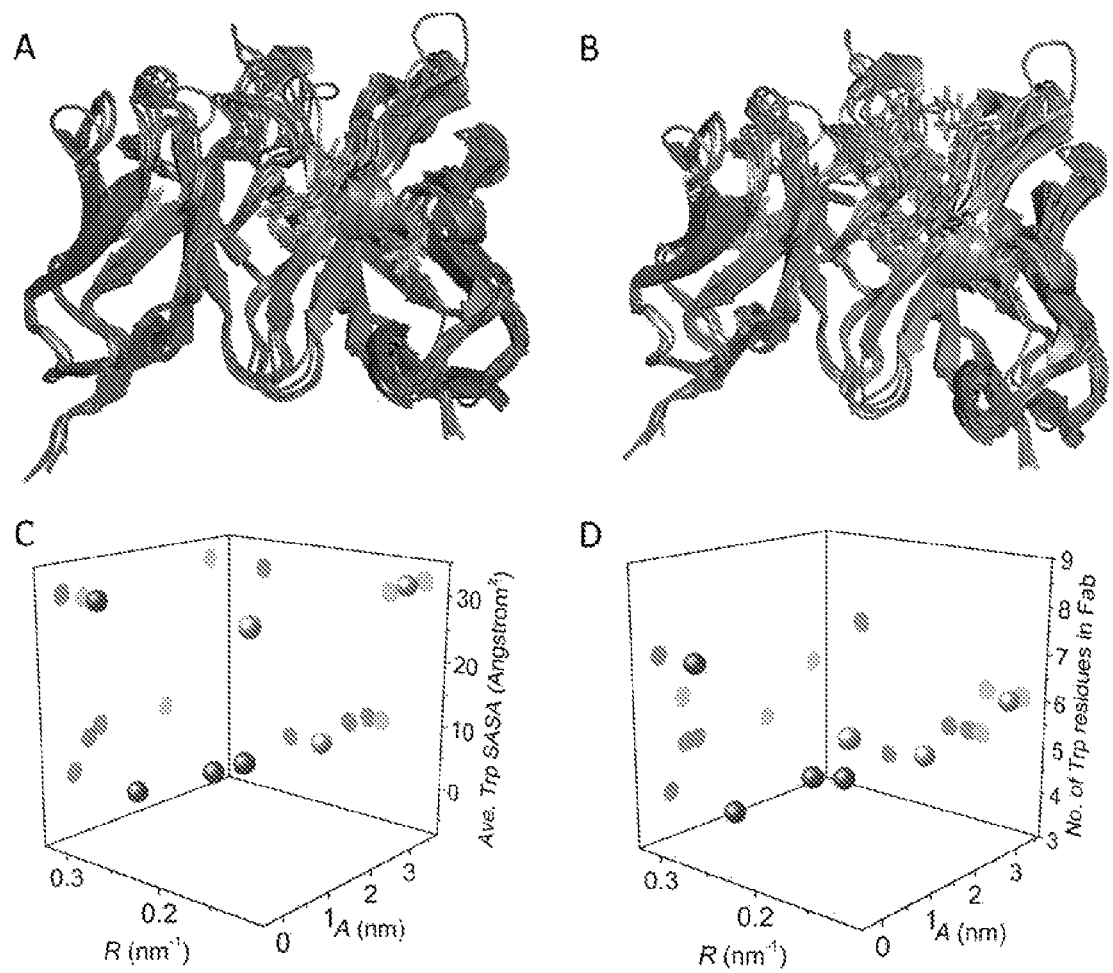
Figure 18 A to D
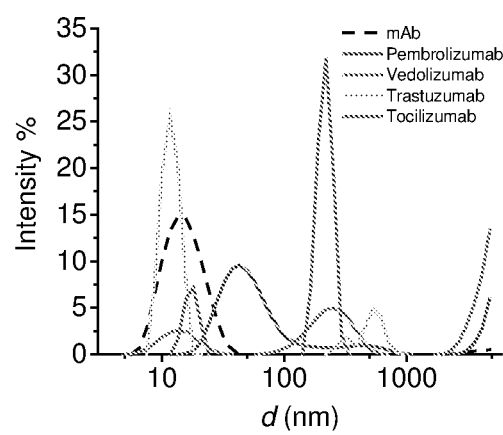
Figure 19

Summary of calculated parameters for mAb Fab regions

|  | Number of Trp residues in the Fab | Average Trp SASA trp (Å$^2$) | Average normalised Trp B-factor | Cumulative frequency of calculated normal modes | All atom flexible motion SVRC |
|---|---|---|---|---|---|
| Chimeric | | | | | |
| Cetuximab | 6 | 31.7 | 0.583 | 456.4 | 0.60 |
| Infliximab | 6 | 29.3 | 0.630 | 444.5 | 0.44 |
| Rituximab | 5 | 8.8 | 0.648 | 394.2 | 0.55 |
| Humanised | | | | | |
| Bevacizumab | 7 | 30.3 | 0.528 | 454.5 | 0.67 |
| Natalizumab | 5 | 8.9 | 0.620 | 392.4 | 0.50 |
| Pertuzumab | 4 | 2.6 | 0.510 | 502.3 | 0.75 |
| Trastuzumab | 5 | 7.4 | 0.639 | 435.8 | 0.56 |

PROTEIN STRUCTURE ANALYSIS BASED ON RED-EDGE EXCITATION SHIFT (REES) SPECTROSCOPY

FIELD OF THE INVENTION

Aspects and embodiments relate to a method, a computer program product and protein structure analysis unit configured to perform the method. Further aspects and embodiments provide protein structure analysis apparatus including a computer program product or protein structure analysis unit configured to perform the method and uses thereof.

BACKGROUND

Proteins are polypeptides formed from sequences of monomer amino acids. Protein structure determines protein function. Proteins may fold into one or more specific spatial conformations driven by various non-covalent interactions, for example, hydrogen bonding, ionic interactions, Van der Waals forces, and hydrophobic packing. Understanding the functionality of a protein at a molecular level may be assisted if it is possible to determine its three-dimensional structure.

It will be understood that proteins are thermodynamically unstable molecules and may be considered to be intrinsically flexible, dynamic molecules able to a sample a range of conformational states. For example, folded and unfolded states of a protein may differ by only the energy of a small number of hydrogen bonds.

Often the conformational plasticity of a protein is an important feature of ligand binding and enzyme activity. Like the folded structure of a protein, protein flexibility may also be thermodynamically unstable. That is to say, small changes in molecular environment or protein interactions may significantly alter the normal flexibility of a protein.

Some proteins, such as antibodies, rely on a native dynamic profile in order to function correctly. The lability of protein dynamics can be a major barrier to research, manufacture and storage of such proteins.

The challenges of developing stable biomolecule formulations and assaying for precise retention of conformation is crucial to the commercial viability and efficacy of biopharmaceuticals. However, the techniques are not yet in place to capture subtle or even major changes to a protein's native dynamic profile. Potential approaches that capture this information include NMR, EPR, single molecule spectroscopy, ion mobility mass spectrometry (IM-MS) and hydrogen/deuterium (H/D) exchange mass spectrometry. However, these approaches are not in routine use due to significant technical complexity and feasibility, instrument expense, time of assay, complex sample preparation and need for specialist analysis.

CHAUDHURI A ET AL: "Organization and dynamics of tryptophans in the molten globule state of bovine alpha-lactalbumin utilizing wavelength-selective fluorescence approach: Comparisons with native and denatured states", BIOCHEMICAL AND BIOPHYSICAL RESEARCH COMMUNICATIONS, ELSEVIER, AMSTERDAM, NL, vol. 394, no 4, 24 Mar. 2010 describes a set of approaches based on the red edge effect in fluorescence spectroscopy that can be used to directly monitor the environment and dynamics around a fluorophore in a complex system. The document states REES arises due to slow rates of solvent relaxation (reorientation) around an excited state fluorophore, which depends on the motional restriction imposed on the solvent molecules in the immediate vicinity of the fluorophore. Using that approach, it becomes possible to probe the mobility parameters of the environment using a fluorophore as a reporter group. The document reports the fluorescence emission spectra of Bovine α-lactalbumin in various conformations and a shift in emission maximum on red edge excitation is shown to be linked to protein conformation.

KLAJNERT B ET AL: "Interactions between PAMAM dendrimers and bovine serum albumin", BIOCHIMICA ET BIOPHYSICA ACTA (BBA)—PROTEINS & PROTEOMICS, ELSEVIER, NETHERLANDS, vol. 1648, no. 1-2, 2003, pages 115-126 studies interactions between PAMAM dendrimers and bovine serum albumin (BSA). The document describes use of bovine serum albumin (containing two tryptophan residues) to evaluate the influence of dendrimers on protein molecular conformation. In particular, the document describes measuring changes in fluorescence of BSA in the presence of dentrimers. REES was used to analyse whether tryptophan residues (in a given PAMAM-BSA interaction) were in a motionally restricted environment.

H. RAGHURAMAN AND CHATTOPADHYAY A: "Effect of ionic strength on folding and aggregation of the haemolytic peptide melittin in solution", BIOPOLYMERS, vol. 83, no. 2, 5 May 2006, pages 111-121 describes a study of the effect of ionic strength on folding and aggregation of the Hemolytic peptide melittin in solution. The study shows that REES may be used as a tool to monitor aggregation behaviour of melittin in particular and other proteins and peptides in general. The document includes results showing the effect of changing excitation wavelength on the wavelength of maximum emission of melittin in aqueous solutions of various strengths. A significant change in the magnitude of REES was observed upon increasing the concentration of NaCl from 0.1 to 1 M. The document attributes the change to an increase in the motional restriction of solvent molecules around excited state tryptophan residues with increasing ionic strength. The document suggests that the REES effect observed is suggestive of salt-induced self association of melittin being coupled to the change in the dynamics of hydration around the tryptophan residue.

It is desired to provide a mechanism to provide information about the conformational structure of a protein.

SUMMARY

Aspects and embodiments recognise that proteins in general and bio-pharmaceutical proteins in particular may have a vast range of commercial, academic and therapeutic applications and that their proper function is often based on protein structure. In particular protein function may depend upon protein flexibility, for example, for antibody recognition of epitopes.

Breakdown in the normal flexibility of proteins is common, for example, under minor temperature changes. Similarly, when manufactured, a protein may display batch to batch variations in flexibility, since flexibility can be the least 'stable' aspect of protein structure. Loss of native flexibility may proceed to unfolding and aggregation. At an industrial scale, variation or loss of protein function as a result of changes to protein structure represents a huge loss in potential revenue and research costs.

Analytical quality control (QC) tools required in relation to bio-pharmaceuticals and other biologics in which structure determines function differ significantly to those required in relation to, for example, purely chemical pharmaceuticals.

Minimum testing requirements for bio-pharmaceuticals may, for example, include: physico-chemical stability and assessment of degradation and sub-visible particles (soluble aggregates).

Aspects and embodiments recognise that an analytical tool which can offer a means to detect when proteins, for example, bio-pharmaceuticals, may have lost their normal conformation and/or flexibility and/or begun aggregating may have significant benefits. Such an analytical tool may be used within industrial manufacturing processes in relation to, for example, QC of proteins—such as antibody batches—and by formulation scientists in order to determine appropriate solvents and buffer ions and the like in which to store proteins, thus creating a stable protein sample. Additionally, end users may use an appropriate analytical tool provided by aspects and embodiments to check, for example, that off the shelf purchased proteins, including antibodies, are still fit for purpose.

Some protein analysis tools can be time consuming, require specialist knowledge, expensive instrumentation and may be highly system-specific. Aspects and embodiments may provide a simple and robust analytical technique that can be used without a need for highly specialized equipment, on a broad range of proteins, and in a variety of settings.

Aspects recognise that it may be possible to use an optical phenomenon to analyse protein structure, and that by observing the characteristics of the optical phenomenon displayed by a protein sample comprising a protein, solvent and buffer, it is possible to determine a fingerprint or characterisation of that protein sample. Aspects and embodiments recognise that the characteristics of the optical phenomenon displayed by a protein sample comprising a protein, solvent and buffer map to particular features of protein structure. Aspects and embodiments may provide a mechanism to characterise a protein sample structure numerically, each numerical characteristic providing an indication of a physical characteristic of the structure of a protein within a protein sample. Furthermore, such numerical analysis may allow for comparison of a protein sample to an "ideal" (for example, a control) protein sample, thus providing a means to assess changes in structure of a protein within a protein sample. Detected changes in structure may offer an indication of the extent to which the protein in the protein sample may provide desired protein function.

Aspects and embodiments recognise that some protein samples may, on excitation with appropriate radiation, emit radiation and that emission may comprise a fluorescence emission spectrum. Aspects and embodiments recognise that, if a protein sample emits a fluorescence spectrum in the event of appropriate stimulation, "edge shifts" in the fluorescence spectra obtained from protein samples may contain information regarding the structure of the protein. Aspects recognise that use of fluorescence phenomena to analyse the structure of a protein sample may allow for protein testing which is extremely rapid, low cost, easy to perform and information rich. Furthermore, such techniques may be non-destructive to the protein sample under test.

For example, some aspects and embodiments may use an optical phenomenon called red edge excitation shift (REES). The REES effect occurs as a result of the fluorescence of molecules and may provide a mechanism to understand both inherent protein sample structure together with how proteins may interact with their surrounding environment. Aspects and embodiments recognise that it is possible to use fluorescence effects exhibited by proteins, such as the REES effect, to accurately report on general characteristics of a protein structure and detect changes in protein flexibility if comparing between batches of a protein or comparing aged protein samples to a fresh protein sample.

Some aspects and embodiments recognize emission arising from, for example, a single Trp residue may give a significant REES effect in a protein when in folded and molten globule like states, but that the REES effect may disappear or be rather reduced in unfolded states. Some aspects and embodiments recognize that edge shift effects, such as the REES effect, may offer a mechanism to probe proteins with a high degree of molecular flexibility resulting in an ensemble of solvent environments around, for example, a Trp probe. In relation to proteins, such an ensemble may arise from a broad equilibrium of conformational states, such as in molten globule intermediates of highly flexible or dynamic proteins.

Typical analysis of fluorescence edge shift effects exhibited by a protein is such that the relationship is assumed to follow a simple linear relationship between applied excitation and resulting fluorescence emission spectra. For example, a simple linear equation is often fitted to experimentally obtained REES data. Aspects and embodiments recognise that such a linear fit is poor. Aspects and embodiments recognise that the curvature in a plot of experimental data may be explained by the underlying physical phenomena and the structure of the protein within the studied protein sample.

Some aspects and embodiments quantify the REES effect by fitting the REES data to a distribution function that captures the innate curvature in REES data. From the fitted distribution function it is possible to extract values for, for example, the relative magnitude of the REES effect ($A_{rel}$) and the centre of spectral mass ($CSM_0$); and aspects and embodiments recognise that those values can be related to inherent structural characteristics of the protein sample being tested. Furthermore, aspects and embodiments recognise that the extracted values may also be independent of excitation wavelength and thus offer a means to characterise or "fingerprint" a protein sample.

Accordingly, a first aspect may provide a method which comprises: receiving a fluorescence emission spectrum generated by a protein sample at a first excitation wavelength, the protein sample being configured to exhibit fluorescence in dependence upon its conformational state. It will be appreciated that not all protein samples may exhibit edge shift fluorescence effects. Accordingly, the first aspect may provide information in relation to proteins which display intrinsic fluorescence as a result of naturally occurring fluorophores within the protein structure, or which have been appropriately configured with extrinsic fluorophores at appropriate sites within the protein structure. In order to obtain useful fluorescence spectra, it will be appreciated that it may be necessary to stimulate or excite a protein sample using light or other radiation having an appropriately selected energy (wavelength) range. In particular, the excitation wavelengths may be chosen having regard to an expected fluorescence response of a given protein sample.

The method may comprise: evaluating, from the fluorescence emission spectrum, an indication characteristic of a fluorescence response of the protein sample at the first excitation wavelength. The indication characteristic of the fluorescence response of the protein sample may comprise an indication of the wavelength at which the emission peak occurs, or the centre of spectral mass of the emission spectrum.

The method may comprise: repeating the receiving and evaluating steps in relation to a plurality of fluorescence emission spectra, each fluorescence spectrum generated by the protein sample at a different excitation wavelength to the first excitation wavelength. Accordingly one protein sample, either the identical protein sample or various protein samples taken from the same source, may be retested, and a series of emission spectra relating to the same protein sample may be used to evaluate an indication representative of a physical characteristic of the protein sample under test. It will be appreciated that the conformational state of the protein sample under test must remain stable throughout the series of emission spectra generated. Accordingly, the temperature and pressure of the protein sample may be controlled. Similarly, the intensity of the radiation causing excitation at the first excitation wavelength and/or subsequent radiation wavelengths may be controlled, to minimise the likelihood of conformational change occurring as a result of the testing or as a result of a change in the ambient environment surrounding the protein sample.

The method may comprise: generating a non-linear relationship between excitation wavelength and indication characteristic of fluorescence response of the protein sample. Having obtained a plurality of fluorescence emission spectra from a protein sample, it may be possible to generate a relationship between the observed macroscopic behaviour of the protein sample system and the likely conformational state of the protein with that protein sample.

The non-linear relationship generated may comprise an indication of at least one characteristic of the conformational state of the protein sample, based upon correlation of the received excitation wavelengths and associated evaluated indications characteristic of the fluorescence response of the protein sample.

Aspects and embodiments provide a fluorescence-based method which may provide a "fingerprint" reflecting the dynamic profile and structure of a protein, for example, an antibody. The fingerprint may, for example, comprise a two-dimensional characterisation. Aspects and embodiments may provide a means to discern between individual types or classes of proteins and/or a means to discern between proteins within a single type or class. Aspects and embodiments may provide a means to discern between proteins with one or more different folds, between proteins in the same or different superfamily, between proteins in the same or different families, between proteins with different protein domains, or between different species of proteins.

Aspects and embodiments may provide a means to discern between proteins with a high level of sequence similarity. As described herein and as illustrated in FIG. 12(c), the present disclosure is effective at discerning or distinguishing between proteins that have a high degree of sequence similarity. Some aspects and embodiments provide for a fingerprint generated in relation to a protein sample to be compared to a fingerprint generated in relation to a protein with a high level of sequence similarity. Such proteins can have at least 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% sequence similarity. Such proteins can have at least 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% sequence similarity. Such proteins can have at least 95%, 96%, 97%, 98%, 99%, 99.1%, 99.2%, 99.3%, 99.4%, 99.5%, 99.6%, 99.7%, 99.8%, 99.9% sequence similarity.

The terms "homology, identity or similarity" refer to the degree of sequence similarity between two polypeptides or between two nucleic acid molecules encoding the two polypeptides as compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (for example, BLOSUM62, PAM250, Gonnet etc.), and gap-penalty, for example, functional form and constants. Having made the alignment, there are different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance. The popular multiple alignment program ClustalW (*Nucleic Acids Research* (1994) 22, 4673-4680; *Nucleic Acids Research* (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

Aspects and embodiments may provide a means to discern between protein variants. A "variant" means a substantially similar sequence. A variant can have a similar function or substantially similar function as a wild-type sequence. A similar function can be at least about 50%, 60%, 70%, 80% or 90% of wild-type enzyme function or at least about 90%, 95%, 96%, 97%, 98% or 99% of wild-type enzyme function. The variants can have one or more mutations that result in the enzyme having a modulated level of activity as compared to the wild-type polypeptide. For example, the variants can be mutant proteins produced by introducing any type of alterations (for example, insertions, deletions, or substitutions of amino acids; changes in glycosylation states; changes that affect refolding or isomerizations, three-dimensional structures, or self-association states), provided that they still have some or all of their function or activity. Such variants can be produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally.

Methods according to some aspects and embodiments may allow, for example, for the capture of subtle shifts away from a native protein structure, and, for example, any shift in native dynamics of a protein. Aspects and embodiments described combine numerical modelling, structure calculation and biophysical analysis to validate the general approach.

Some aspects and embodiments use the REES effect to provide a quantitative understanding of biomolecular edge shift (QUBES). The QUBES method may allow REES measurements gathered in relation to a protein sample to yield a 2D spectral fingerprint. Some aspects and embodiments provide for a fingerprint generated in relation to a protein sample to be compared to a reference fingerprint in a pre-gathered protein sample reference library to determine the quality of the protein sample being studied.

The 'quality' of the protein sample may relate to, but is not limited to, one or more of the conformational state of the protein in said protein sample, the crowding of the protein in the protein sample, the physical compactness of the protein in the protein sample; the stability of the protein in the protein sample; and/or the aggregation of the protein in the protein sample.

Some aspects and embodiments relate to detecting protein unfolding and/or formation of protein aggregates—including soluble protein aggregates.

Some aspects and embodiments relate to quantifying protein unfolding and/or formation of soluble aggregates—including soluble protein aggregates.

Some aspects and embodiments relate to predicting sample stability.

The methods described herein can have a number of advantages, including: (i) data acquisition and analysis is rapid (<5 mins) so can be used as part of large scale screening; (ii) it can be used with any protein which includes one or more Trp residues (most proteins); (iii) it can be used with proteins of any size and in nearly any solvation/buffer environment; (iv) the measurements can be high-throughput (96 well plate); (v) samples are not consumed; (vi) the approach requires only a low sample concentration; and (vii) a single value captures a complete set of information on the proteins conformation. Aspects and embodiments recognise that use of fluorescence effects to analyse the structure of a protein may have various advantages including, for example, that: (i) data acquisition and analysis is rapid (<5 mins) so can be used at a point of use; (ii) it can be used with any protein which includes one or more naturally occurring fluorescent amino acids (intrinsic fluorophores), and particularly those with Trp residues (most), or proteins having appropriately selected extrinsic fluorophores; (iii) it can be used with proteins of any size and in nearly any solvation/buffer environment; (iv) the measurements can be high-throughput; (v) samples are not consumed; and (vi) the approach typically requires only a small sample concentration.

In some embodiments, the indication of at least one characteristic of the conformational state of the protein sample comprises: an indication of a number of discrete conformational states of a protein in the protein sample. Accordingly, in some embodiments, the indication of at least one characteristic of the conformational state of the protein sample comprises: an indication of a free energy landscape of a protein in the protein sample. In other words, the fluorescence spectra produced by a protein sample may provide an inherent indication of the ruggedness of the free energy landscape of a protein sample.

In some embodiments, the indication of at least one characteristic of the conformational state of the protein sample comprises: an indication of a magnitude of curvature of the relationship between excitation wavelength and indication characteristic of fluorescence response of the protein sample. In particular, the curvature of the relationship between excitation wavelength and indication characteristic of fluorescence response of the protein sample provides an indication of the magnitude of the fluorescence edge effect, for example, REES effect, displayed by a protein sample. The magnitude of that effect may provide an inherent, relative or comparative indication of the nature, for example, number, of conformational states available to the protein in the protein sample. Accordingly, the magnitude of the observed fluorescence edge shift effect may provide an indication of the "ruggedness" of the free energy landscape of a protein in a protein sample.

In some embodiments, the indication of at least one characteristic of the conformational state of the protein sample comprises: an indication of a relative folded or unfolded nature of the conformational state of a protein in the protein sample. In some embodiments, the indication of at least one characteristic of the conformational state of the protein sample comprises: an indication of crowding of a protein in the protein sample.

In some embodiments, the indication of at least one characteristic of the conformational state of the protein sample comprises: an indication of physical compactness of a protein in the protein sample.

In some embodiments, the indication of at least one characteristic of said conformational state of said protein sample comprises: an indication of stability of a protein in said protein sample.

In some embodiments, the indication of at least one characteristic of said conformational state of said protein sample comprises: an indication of aggregation of a protein in said protein sample. In some embodiments, the indication of at least one characteristic of the conformational state of the protein sample comprises: an indication of the indication characteristic of fluorescence response which is determined to be independent over a range of excitation wavelength. Accordingly, across a wide range of excitation wavelengths, the fluorescence response of a protein sample may be substantially uniform. That base fluorescence response may provide information about the inherent, comparative or relative folded nature of a protein within a protein sample.

In some embodiments, the non-linear relationship between excitation wavelength and indication characteristic of fluorescence response of the protein sample comprises: an exponential function, or a symmetric or asymmetric exponential probability function. The relationship may comprise a Gaussian, skewed Gaussian, or sum of exponentials. Such mathematical or numerical "models" for protein samples match the general shape of the expected physical behaviour of a protein configured to exhibit fluorescence effects.

In some embodiments, the non-linear relationship between excitation wavelength and indication characteristic of fluorescence response of the protein sample comprises: a Gaussian probability distribution of the form:

$$f(x) = R_0 + \frac{A\sqrt{2/\pi}}{w}\exp\left(-2\left(\frac{x-m}{w}\right)^2\right) \quad \text{Eq 2.}$$

Where A is the area, w is the full width at half-maximal (fwhm), m is the mid-point and $R_0$ is the y-intercept and $m=\lambda_{REES}^{max}$, where $\lambda_{REES}^{max}$ is the excitation wavelength that gives the largest change in the fluorescence emission peak wavelength.

In some embodiments, the protein sample comprises: a protein, solvent and buffer, and the indication of at least one characteristic of the conformational state comprises an indication of the conformational state of the protein in the solvent and buffer. It will be understood that the conformational state(s) taken by a protein will depend upon concentration of protein, solvent and buffer within a protein sample and that the fluorescence of a protein sample will depend on the solvation state of a protein.

In some embodiments, the indication of the indication characteristic of fluorescence response which is determined to be independent over a range of excitation wavelength, and the indication of a magnitude of curvature of the relationship between excitation wavelength and indication characteristic of fluorescence response of the protein sample, comprise a fingerprint characteristic of the protein sample. Accordingly, for a given protein sample, it may be possible to determine a fingerprint, or characteristic indicative of, for example, the free energy landscape or "ruggedness" of a protein sample and the "folded-ness" of a protein sample in a native form. Such a fingerprint may be generated by testing a protein sample immediately after manufacture. Comparison of the fingerprint of an "identical" protein sample, for example, a protein sample from that batch, some time after manufacture may offer an indication of whether that protein sample has a similar enough conformation (structure) to still function as intended at the point of manufacture. The fingerprint may comprise two or more values characteristic or indicative of a characteristic of the protein sample. In other words, the fingerprint may be two dimensional, three dimensional of multi-dimensional.

In some embodiments, the method comprises: generating the indication of at least one characteristic of the conformational state of the protein sample for a plurality (for example, two or more) of different protein samples. Accordingly, it may be possible to generate a look up table comprising at least one "ideal" indication in relation to one or more protein samples.

In some embodiments, the method comprises: generating the indication of at least one characteristic of the conformational state of the protein sample for a plurality (for example, two or more) of different protein samples that have a high degree of sequence similarity, as discussed herein.

In some embodiments, the method comprises: comparing the indication of at least one characteristic of the conformational state of the protein sample with a previously generated indication of at least one characteristic of the conformational state of a further protein sample. Accordingly, the further protein sample may be compared against determined characteristics of a protein sample, or set of protein samples, for which the indication of at least one characteristic of the conformational state of the protein sample is known, to identify the further protein sample. That is to say, the further protein sample may be compared against a look up table in relation to one or more "known" protein samples for the purposes of identification of the further protein sample.

In some embodiments, the method comprises: comparing the indication of at least one characteristic of the conformational state of the protein sample with a previously generated indication of at least one characteristic of the conformational state of an identical protein sample. Accordingly, a protein sample may be compared against determined characteristics of an "ideal" (for example, a control) protein sample to determine whether it may still have a structure which is deemed fit for purpose. Such arrangements may allow a mechanism to perform non-destructive QC testing in relation to a protein sample.

In some embodiments, the method comprises: comparing the indication of at least one characteristic of the conformational state of the protein sample, with an indication of at least one characteristic of the conformational state of a protein sample comprising the same protein having one or more different: concentration, solvent and buffer. Accordingly, since methods may allow for inherent properties of a protein sample to be determined, the method may allow formulation scientists to identify, by means of comparison between protein samples, a stable storage (solvent and buffer) for a given protein, thus allowing for increased likely usable biologic protein lifetimes.

In some embodiments, the protein sample comprises: a protein including at least one intrinsic fluorophore. In some embodiments, the intrinsic fluorophore comprises: tryptophan.

In some embodiments, the protein sample comprises a protein including at least one extrinsic fluorophore. A second aspect provides a computer program product operable, when executed by a computer, to perform the method of the first aspect.

A third aspect provides a protein structure analysis unit according to claim 22.

The protein structure analysis unit of the third aspect may be appropriately configured to provide and perform any of the features and methods described in more detail in relation to embodiments of the first aspect.

A fourth aspect may provide a protein structure analysis apparatus comprising: a sample holder configured to receive a protein sample; a controllable light source operable to excite the protein sample; a detector operable to receive a fluorescence emission spectrum produced by the protein sample; and a control unit configured to communicate with the controllable light source and detector, the control unit comprising a protein structure analysis unit in accordance with the third aspect.

A fifth aspect may provide the use of the protein structure analysis unit according to the third aspect for determining an indication of a relative folded or unfolded nature of a protein, or for determining an indication of crowding of a protein; or for determining an indication of physical compactness of a protein, or for determining an indication of stability of a protein; or for determining an indication of aggregation of a protein; or for selecting an optimal protein formulation; or for monitoring protein stability, folding or aggregation Various applications of aspects and embodiments are envisaged, including, for example, QC of manufactured proteins—such as bio-pharmaceutical proteins and/or recombinant proteins.

A sixth aspect may provide a method for comparing the stability of two or more protein samples comprising: providing two or more protein samples; performing the method according to the first aspect on each of said protein samples; and comparing the stability of the two or more proteins, wherein a difference in the indication of at least one characteristic of said conformational state of each of said proteins is indicative of a difference in stability.

A seventh aspect may provide a method for comparing the stability of two or more protein samples comprising: providing a protein sample; performing the method according to the first aspect on said protein sample; and comparing the stability of the protein against the stability of a second protein sample on which the method according to the first aspect has been carried out, wherein a difference in the indication of at least one characteristic of said conformational state of each of said proteins is indicative of a difference in stability.

An eighth aspect may provide a method for formulating a protein preparation with increased stability comprising: providing a protein in a protein sample; performing the method according to the first aspect on said protein sample in the presence of one more agents that modulate the stability of the protein; selecting one or more agents that increase the stability of the preparation in comparison to the stability of the preparation in the absence of the one or more agents; and formulating the protein preparation.

A ninth aspect may provide a method for monitoring protein stability, folding or aggregation over time comprising: providing a protein in a protein sample; and performing the method according to the first aspect on said protein at two or more different time points; wherein a difference between the results from the two or more different time points is indicative of a change in protein stability, conformation or aggregation of the protein over time.

A tenth aspect may provide a method for identifying one or more agents that modulate protein aggregation or protein folding comprising: providing a protein in a protein sample; performing the method according to the first aspect on said protein sample in the presence and absence of one or more test agents that may modulate the aggregation of folding of the protein; and selecting one or more agents that modulate the aggregation or the folding of the protein, wherein a difference in the level of aggregation or folding in the presence of the test agents is indicative that the test agent modulates protein aggregation or folding. Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIGS. 1a and 1b illustrate how an example protein, NEMO W6, displays a significant REES effect;

FIG. 1a is a contour plot showing the change in structure of emission spectra with increasing $\lambda_{Ex}$. The dashed line of FIG. 1a illustrates the change in the $\lambda_{Em}^{max}$ for each emission spectrum and is provided as an aid to the eye only;

FIG. 1b illustrates schematically relative change the intensity of W6 emission ($\lambda_{Em}^{max}$ shown as a dashed line to aid the eye) for increasing $\lambda_{Ex}$.

FIG. 1b (inset) illustrates schematically the corresponding change in CSM with $\lambda_{Ex}$ together with an example calculated a linear fit;

FIG. 2 illustrates a phenomonological model which fits REES data. The excitation spectrum of NEMO W6 (emission at 348 nm) is shown as a grey line (right-hand axis) across an extended wavelength range. The variation in CSM with $\lambda_{Ex}$ for NEMO W6 is shown as black circles (left-hand axis) and the solid line is an example curved fit line comprising a sum of two Gaussians which capture the ascending and descending limb of the experimentally obtained REES data;

FIG. 3 illustrates graphically the effect of denaturation and crowding on NEMO REES data. The REES data for native NEMO (black circles), denatured NEMO (red circles) and crowded (20 mg/ml Sbi) NEMO are fit to an example curved fit line comprising a sum of two Gaussians which capture the ascending and descending limb of the experimentally obtained REES data. The inset shows the extracted value of A from the example curved fit line, and is indicative of the curvature of the REES data;

FIG. 4 illustrates graphically that he REES effect is sensitive to pressure variation;

FIG. 4a illustrates graphically variation in REES with increasing pressure. Dashed lines are the fits to an example curved fit line comprising a sum of two Gaussians which capture the ascending and descending limb of the experimentally obtained REES data;

FIG. 4b illustrates graphically the pressure dependence of A extracted from the fits of data shown in FIG. 4a;

FIG. 5 illustrates graphically a conceptual framework for interpretation of tryptophan REES data in proteins;

FIG. 6 illustrates graphically ligand induced conformational change occurs by altering the existing equilibrium of NEMO conformational states;

FIG. 6a illustrates graphically a change in REES data on binding IκBα and IKK-β peptides; the solid line in each instance comprises the fit to an example curved fit line comprising a sum of two Gaussians which capture the ascending and descending limb of the experimentally obtained REES data. The Inset illustrates graphically the extracted relative magnitude of A from the fit;

FIG. 6b illustrates graphically a change in REES data on binding different poly-ubiquitin chain lengths; the solid line is the fit to an example curved fit line comprising a sum of two Gaussians which capture the ascending and descending limb of the experimentally obtained REES data. The Inset illustrates graphically the extracted relative magnitude of A from the fit;

FIG. 7a illustrates the emission spectrum of tyrosine excited at 292 nm. The raw spectra, buffer spectra and difference spectrum are shown;

FIG. 7b illustrates the emission spectrum of 2 μM NEMO and 10 μM tyrosine (from A) excited at 292 nm. The total emission of Tyr is 0.5% of the total NEMO emission;

FIG. 7c illustrates the emission spectrum of NEMO excited at 292 nm (black line; left axis) and 310 nm (blue line; right axis). The grey and cyan lines show the subtraction of the emission spectrum of 10 μM Tyr from the NEMO emission spectra at 292 nm and 310 nm, respectively;

FIG. 7d illustrates the resulting REES effect for NEMO (black) and for the Tyr subtracted spectra for 10 μM Tyr (red).

FIG. 8 illustrates that Sbi does not display a significant REES effect;

FIG. 8b Inset illustrates graphically the corresponding change in CSM with $\lambda_{Ex}$ calculated from a linear fit;

FIG. 9 illustrates the pressure-dependnece of free Trp emission is neglibable compared to NEMO W6 and does not show a REES effect;

FIG. 10b illustrates various emission spectra obtained from the protein sample of FIG. 10a;

FIG. 10c illustrates graphically a comparison of emission wavelength (x-axis) to excitation wavelength (y-axis) for the protein sample of FIG. 10a;

FIG. 11 illustrates schematically main component parts of apparatus configured to record optical shift phenomena in some arrangements;

FIGS. 12a to 12C provide an overview of protein structure and analysis according to an arrangement which uses the REES effect as a specific reporter of mAb structure;

FIG. 12a illustrates schematically a general structure of the fragment antigen-binding (Fab) region of a range of mAbs;

FIG. 12b illustrates schematically example REES data for a mAb and shows and arrangement in which a Gaussian function is fitted to empirical data;

FIG. 12C illustrates schematically one example plot of parameters extracted from a Gaussian function fitted to empirical data as in FIG. 12b for a series of different mAbs;

FIG. 16A to D shows how QUBES can be used to predict thermodynamic stability;

FIG. 17 shows the different detection capabilities of QUBES; and

FIG. 18-21 are supporting Figures.

DESCRIPTION OF THE EMBODIMENTS

Figures 7A, 7B, 7C, 7D:
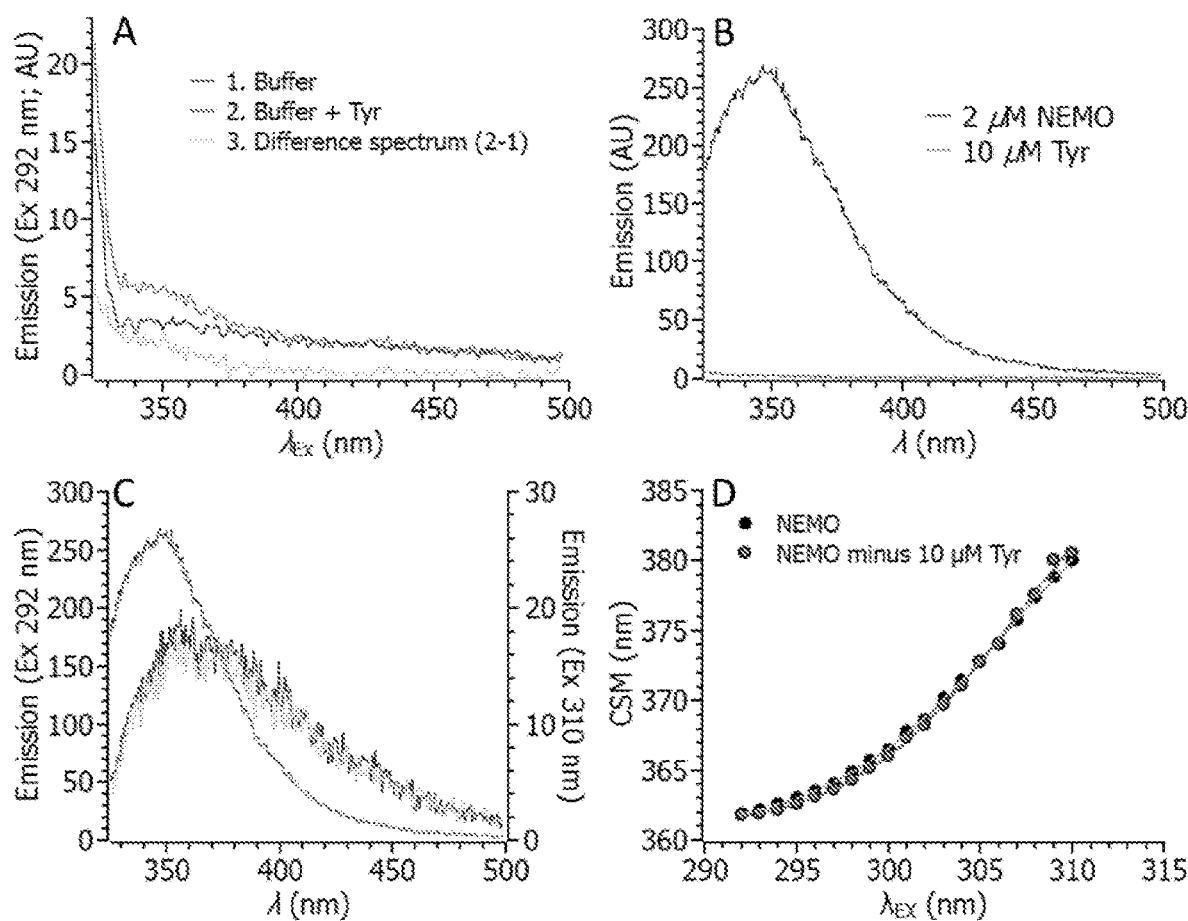
FIGS. 7a to 7d comprise background supporting experimental data.

Unless defined otherwise, all technical and scientific terms used herein have the same meaning as commonly understood by those of ordinary skill in the art, such as in the arts of physical chemistry, protein chemistry, protein biology and biochemistry. Unless otherwise indicated, standard techniques are used for chemical and biochemical methods.

Before describing arrangements in detail, a general overview is provided. It is recognized in the study of proteins, and in particular biological proteins such as antibodies, that to understand complex molecular interactions it is helpful to account for molecular flexibility and the available equilibrium of conformational states.

NMR techniques are understood to provide the best images of protein structures in terms of resolution, but NMR techniques require specialist equipment and take significant time. It is desirable to provide a structural analysis tool which is fast and can provide information relating to molecular flexibility. It is recognized that regardless of the level of protein structure being considered (quaternary, tertiary, secondary) the first thing to 'denature' is the normal flexibility of the molecule.

The flexibility of a protein is coded into the fold by the primary sequence and is also affected by the environment surrounding the protein, for example, solvent viscosity, salinity, pH, crowding and similar. The native flexibility of a protein may break down very easily, for example, as a result of small changes in temperature, viscosity, pH, protein concentration and similar. It is recognized that protein flexibility is related to different protein functions including, for example, ligand binding, enzyme activity, cellular localisation.

There is an increasing realization that the molecular mechanism of many human proteins, particularly those involved in signaling networks, are governed by molecular flexibility and protein structural disorder. That is, proteins that mediate multiple signaling inputs may fold into ligand specific conformations, providing high specificity to a large number of structurally dissimilar ligands [1]. Underpinning these notions is the free energy landscape (FEL) model of protein structure, which interprets molecular heterogeneity (structural disorder and flexibility) as a series of equilibrated energetic minima on a multi-dimensional free energy surface [2]. Proteins that are highly flexible or exist as significantly different discrete conformational states are considered to have a rather 'rugged' FEL. For signaling proteins, understanding how the FEL is altered on ligand binding is key to understanding the molecular mechanism of biological signaling networks.

Detecting ligand induced conformational change (folding) and the relationship to the equilibrium of protein conformational states is challenging. EPR [3] single molecule (SM) [4,5]. Ion mobility mass spectrometry (IM-MS) [6] and NMR [7] studies can be used for this purpose with different levels of resolution.

Arrangements recognize that edge shifts on fluorescence emission spectra generated by a protein sample (for example, protein in an appropriate solution, together with appropriate buffer ions) may provide information regarding protein structure. Experimental arrangements described further below demonstrate that one possible edge shift of use may comprise an optical phenomenon called Red Edge Excitation Shift (REES). REES of a protein sample may provide unique information on protein conformational change and the equilibrium of conformational states [8].

Generally, arrangements explore optical physics techniques which monitor emission of fluorophores by a protein sample. In other words, aspects recognize that it is possible to use fluorescence spectra of a protein sample to characterize the physical configuration of that protein sample.

Any kind of test protein is contemplated for use in the present disclosure provided that it can be analysed by optical methods. To demonstrate the possibility of using optical methods to assess protein flexibility, it has been recognized that many proteins have a very convenient naturally occurring (intrinsic) fluorphore (tryptophan) which is very bright and responds to changes in its environment. Tryptophan (Trp) residues in proteins are extremely sensitive reporters of the immediate molecular environment. Trp residues can display a shift in their emission maximum with a decreasing energy of excitation, because the lower energy photons selectively excite discrete conformational states of the Trp-solvent system, the so called red edge excitation shift (REES) effect. The Trp REES effect is a powerful tool that informs on the dynamic profile of proteins by reflecting the equilibrium of protein conformational states characterised by a proteins free energy landscape (FEL). This approach can therefore be developed to deliver sensitive detection of changes in a proteins dynamic profile as well as overall conformation. The observed REES effect for multi-Trp proteins, can act as a highly accurate fingerprint reflecting subtle differences in both three-dimensional structure as well as protein flexibility.

Antibodies, including monoclonal antibodies (mAbs), are one example of test proteins that can be used in accordance with the present disclosure since they rely on native protein flexibility for function; and are generally structurally similar so identifying one characteristic which is slightly variable may be comparable across test antibodies to identify any trends in obtained experimental data. Furthermore, antibodies typically contain numerous Trp residues which are spectroscopically amenable and show emission changes with changes in surrounding environment. The term "antibody" is used in its broadest sense and covers mAbs, polyclonal antibodies, dimers, multimers, multispecific antibodies (eg. bispecific antibodies), veneered antibodies, antibody fragments and small immune proteins (SIPs) (see, for example, Int. J. Cancer (2002) 102, 75-85). An antibody can include a full-length immunoglobulin molecule or an immunologically active portion of a full-length immunoglobulin molecule, ie. a molecule that contains an antigen binding site that immunospecifically binds an antigen of a target of interest or part thereof. The antibodies may be of any type—such as IgG, IgE, IgM, IgD, and IgA—and any class—such as lgG1, lgG2, lgG3, lgG4, lgA1 and lgA2- or subclass thereof. The antibody may be or may be derived from murine, human, rabbit or from other species.

The antibody may be a complete antibody or an antibody fragment. An antibody fragment refers to a portion of a full length antibody, generally the antigen binding or variable region thereof. Examples of antibody fragments include, but are not limited to, Fab, Fab', F(ab')2, and Fv fragments; diabodies; linear antibodies; single domain antibodies, including dAbs, camelid VHH antibodies and the IgNAR antibodies of cartilaginous fish. Antibodies and their fragments may be replaced by binding molecules based on alternative non-immunoglobulin scaffolds, peptide aptamers, nucleic acid aptamers, structured polypeptides comprising polypeptide loops subtended on a non-peptide backbone, natural receptors or domains thereof.

mAbs are of particular interest in the present disclosure. mAbs are specific, being directed against a single antigenic site and being directed against a single determinant on the antigen. mAbs may be prepared by the hybridoma method described in Nature (1975) 256:495, or they may be made by recombinant DNA methods or they may be isolated from phage antibody libraries as described in J. Mol. Biol. (1991), 222:581-597. The mAb may even be a "chimeric" antibody in which a portion of the heavy and/or light chain is identical with or homologous to corresponding sequences in antibodies derived from a particular species or belonging to a particular antibody class or subclass. The remaining chain(s) is identical with or homologous to sequences in antibodies derived from another species or belonging to another antibody class or subclass, as well as fragments of such antibodies, so long as they exhibit the desired biological activity (see PNAS (1994) USA, 81:6851-6855).

The antibody may be a 'humanised antibody' ie. human immunoglobulins in which residues from a hypervariable region of the recipient are replaced by residues from a hypervariable region of a non-human species (see Curr. Op. Struct. Biol. (1992), 2:593-596). The antibody may be a 'veneered antibody'. This refers to non-human or humanized (eg. chimeric or CDR-grafted antibodies) antibodies that have been engineered to replace certain solvent-exposed amino acid residues so as to reduce their immunogenicity or enhance their function. The antibody may be a bispecific antibody which may comprise a hybrid immunoglobulin heavy chain with a first binding specificity in one arm, and a hybrid immunoglobulin heavy chain-light chain pair (providing a second binding specificity) in the other arm. The antibody may be a human engineered antibody.

The antibody may be a functionally active fragment, derivative or analogue of an antibody that immunospecifically binds to a desired antigen and which still recognises the same antigen that the antibody from which the fragment, derivative or analogue was derived. Suitable fragments of antibodies may include F(ab')2 fragments (which comprise the variable region, the light chain constant region and the CH1 domain of the heavy chain) and Fab fragments, heavy chain and light chain dimers of antibodies, or any minimal fragment thereof such as Fvs or single chain antibodies (SCAs), single domain antibodies (dAbs, IgNAR, VHH) or any other molecule with the same specificity as the antibody.

Derivatives and analogues of antibodies are also contemplated and may include those that have been further modified by, for example, glycosylation, acetylation, pegylation, phosphorylation, amidation and/or derivatization by known protecting/blocking groups, proteolytic cleavage, linkage to a cellular antibody unit or other protein. Chemical modifications may be carried out by known techniques—such as specific chemical cleavage, acetylation and/or formylation.

Additionally, the analogue or derivative may contain one or more unnatural amino acids.

The antibody may be a fusion protein of an antibody, an antibody-drug conjugate, or a functionally active fragment of an antibody, for example, in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies may be commercially obtained from a wide variety of known sources. For example, a variety of antibody secreting hybridoma lines are available from the American Type Culture Collection (ATCC, Manassas, Va.). A large number of antibodies against various disease targets have been deposited at the ATCC and/or have published variable region sequences.

In one embodiment, the antibody is a human mAb.

The protein or antibody can be linked to a drug. It can be a therapeutic protein or antibody. The drug can be a cytotoxic agent that inhibits or prevents the function of cells and/or causes destruction of cells. Examples of cytotoxic agents include radioactive isotopes, chemotherapeutic agents, and toxins such as small molecule toxins or enzymatically active toxins of bacterial, fungal, plant or animal origin, including synthetic analogues and derivatives thereof.

Suitably, the protein for use in the present disclosure is in purified or isolated form, which includes a protein identified and separated and/or recovered from a component of its natural environment. Thus, an isolated or purified protein is substantially free of other cellular material or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. Suitably, the protein will be purified to greater than 90% by weight or 95% by weight as determined by the Lowry method, and most suitably, to more than 99% by weight, or to homogeneity by SDS-PAGE under reducing or non-reducing conditions using Coomassie blue or, preferably, silver stain. Ordinarily, purified or isolated protein will be prepared by at least one purification step. The purification of the protein may include an affinity column containing agents which will bind to the protein; one or more column steps over such affinity resins; one or more steps involving hydrophobic interaction chromatography; or immunoaffinity chromatography. Alternatively, the protein may also be expressed in a form that will facilitate purification. For example, it may be expressed as a fusion protein, such as those of maltose binding polypeptide, glutathione-5-transferase, his-tag or thioredoxin. The protein may be tagged with an epitope and subsequently purified by using a specific antibody directed to such epitope. One or more liquid chromatography steps—such as reverse-phase high performance liquid chromatography can be employed to further purify the protein. Some or all of the foregoing purification steps, in various combinations, can be employed to provide a substantially homogeneous protein. In certain embodiments, the same protein is used but in different formulations or at different time points or in the presence of different agents and the like.

One particular application of the present disclosure relates to the QC of manufactured proteins—such as bio-pharmaceutical proteins and/or recombinant proteins. All biological production systems are susceptible to genetic changes through mutation and foreign genes inserted into host cells may exhibit increased genetic instability. Proteins expressed in foreign hosts may deviate structurally, from their original, originally intended or natural counterparts. These changes can arise at the posttranslational level or during production or purification of the protein and may result in the protein having a change in stability or a change in its aggregation behaviour and the like. This may lead to undesirable effects—including undesirable clinical effects. This may happen over the course of time. In addition, the extensive "scale-up" of fermentation and/or purification that can occur during the scale up to full scale commercial production, can have considerable consequences on the quality of the protein product including effects on conformational structure and aggregation and the like. Maintenance of biological activity both during and after manufacture is generally dependent on molecular conformation of the protein. Proteins can also be particularly sensitive to environmental factors—such as temperature changes, oxidizing factors, light exposure, and storage conditions. Proteins can also be particularly sensitive to changes in formulation. Tests performed at the protein level using the aspects and embodiments of the present disclosure can be used to test or compare the protein product that is produced. Optionally, the protein product can be compared to known (for example, control) protein products to determine the degree of variance therefrom. Optionally, the protein product can be compared to a fingerprint for a known (for example, control) protein product to determine the degree of variance therefrom. Optionally, the protein product may be compared to a look up table comprising at least one "ideal" indication in relation to one or more protein samples to determine the degree of variance therefrom. Optionally, the protein product may be compared over time. Based on the degree of variance that is obtained, a decision can be made whether or not the stability/quality of the protein product is acceptable. Advantageously, the aspects and embodiments of the present disclosure can be carried out at various stages or times of the manufacturing process to monitor the stability/quality of the protein product before and/or during and/or at the end of production. Advantageously, the aspects and embodiments of the present disclosure can be carried out at the end of production to determine the impact of storage conditions/time on the protein.

Other applications of aspects and embodiments are envisaged, including, for example, testing the design and/or re-design of proteins—such as bio-pharmaceutical proteins and/or recombinant proteins. The design and/or re-design may involve the use of genetic changes through mutation which can alter protein conformation/stability and/or protein aggregation. The design and/or re-design may involve the attachment of another molecule to the protein—such as a drug—which can affect protein conformation/stability and/or aggregation. Tests performed at the protein level using the aspects and embodiments of the present invention can be used to determine the impact of the design and/or re-design on the protein. If it is determined that the design and/or re-design of the protein negatively impacts the protein then further changes can be made to optimise the design and/or re-design of the protein.

The methods described herein can be used to decipher if the change in formulation of a pharmaceutical salt has an impact on the quality of the protein. Pharmaceutically-acceptable salts are well known to those skilled in the art, and for example include those mentioned by Berge et al, in *J. Pharm. Sci.* 66, 1-19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts. When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

The methods described herein can be used to decipher if the formulation of a protein into a composition (for example, a pharmaceutical composition) such as by mixing with one or more formulating agents (for example, a suitable carrier, diluent and/or excipient or the like)—has an impact on the quality, stability or conformation of the protein. Suitably, the formulation will maintain or modulate (eg. increase) the quality, stability or conformation of the protein. Suitably, the formulation will decrease aggregation or the likelihood of aggregation of the protein. The composition may be for human or animal usage in human and veterinary medicine and will typically comprise any one or more of a pharmaceutically acceptable diluent, carrier, or excipient. Carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s). Examples of carriers include lactose, starch, glucose, methyl cellulose, magnesium stearate, mannitol, sorbitol and the like. Examples of diluents include ethanol, glycerol and water. Examples of binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used. There may be different composition/formulation requirements dependent on the intended mode of delivery. The composition may be used in combination with a cyclodextrin or a derivative thereof. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Other factors that impact a formulation include buffer composition, pH, salt concentration and the like.

Accordingly, a further aspect relates to a method for formulating a protein preparation comprising: providing a protein in a protein sample; performing the method according to the present disclosure on said protein in the presence of one more formulating agents; selecting one or more agents that maintain or modulate (eg. increase) the quality, stability or conformation of the protein preparation in comparison to the quality, stability or conformation of the protein preparation in the absence of the one or more formulating agents; and optionally formulating the protein preparation.

A still further aspect relates to a method for formulating a protein preparation comprising: providing a protein in a protein sample; performing the method according to the present disclosure on said protein in the presence of one more formulating agents; selecting one or more agents that decreases aggregation or the likelihood of aggregation of the protein preparation in comparison to the aggregation or the likelihood of aggregation of the protein preparation in the absence of the one or more formulating agents; and optionally formulating the protein preparation.

A still further aspect relates to a method for selecting an optimal protein formulation comprising: providing batches of a protein containing different formulating agents; performing the method according to the present disclosure on said batches of protein in the presence of one more formulating agents; selecting one or more formulating agents that maintains or modulate (eg. increase) the quality, stability or conformation of the protein in comparison to the quality, stability or conformation of the protein in the absence of the one or more formulating agents; and optionally formulating the protein preparation.

A still further aspect relates to a method for selecting an optimal protein formulation comprising: providing batches of a protein containing different formulating agents; performing the method according to the present disclosure on said batches of protein in the presence of one more formulating agents; selecting one or more formulating agents that decreases aggregation or the likelihood of aggregation of the protein in comparison to the aggregation or the likelihood of aggregation of the protein in the absence of the one or more formulating agents; and optionally formulating the protein preparation.

The present disclosure can also be used to test proteins over time—such as in batch testing of bio-pharmaceuticals and the like. Proteins will often be stored for an amount of time post manufacture and before use and they often need testing on one or more occasions to monitor their activity. Over time, it is common for proteins to lose activity or come out of solution and/or aggregate.

Accordingly, in a further aspect there is provided a method for monitoring protein confirmation, stability and/or folding/unfolding over time comprising providing a protein in a protein sample; and performing the method according to the present disclosure on said protein at two or more different time points; wherein a difference between the results from the two or more different time points is indicative of a change in the activity of the protein over time.

Other applications of aspects and embodiments include investigating protein aggregation. For example, protein aggregation that may occur during storage or the role of protein aggregation in proteins involved in disease—such as protein aggregation in amyloidogenic proteins involved in neurodegenerative disease—can be investigated. Given the very high sensitivity of the aspects and embodiments described herein to detect protein soluble protein aggregates, the use of the approach may deliver novel ways of monitoring or detecting protein aggregation that may occur during storage or protein aggregation that can occur in diseases and/or offering insight into the formation of these potentially toxic species. Aspects and embodiments also relate to identifying agents that can modulate (for example, decrease) protein aggregation—such as during storage or in disease. Aspects and embodiments therefore also relate to methods for identifying one or more test agents that modulate protein aggregation or protein folding. As used herein, the term "agent" may refer to a single entity or a combination of entities. The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof. The agent may even be a polynucleotide molecule—which may be a sense or an anti-sense molecule. The agent may even be an antibody or a part or parts thereof. The agent may be designed or obtained from a library of compounds, which may comprise peptides, as well as other compounds, such as small organic molecules. By way of example, the agent may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a derivatised agent, a peptide cleaved from a whole protein, a peptide synthesised synthetically (such as, by way of example, either using a peptide synthesizer or by recombinant techniques) or combinations thereof, a recombinant agent, an antibody, a natural or a non-natural agent, a fusion protein or equivalent thereof and mutants, derivatives or combinations thereof. The agent may be an organic compound. Typically the organic compounds may comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. The agent may comprise at least one cyclic group. The cyclic group may be a polycyclic group, such as a non-fused polycyclic group. The agent may comprise at least one of said cyclic groups linked to another hydrocarbyl group. The agent may contain halo groups. The agent may contain one or more of alkyl, alkoxy, alkenyl, alkylene and alkenylene groups—which may be unbranched- or branched-chain. The agent may be in the form of a pharmaceutically acceptable salt—such as an acid addition salt or a base salt—or a solvate thereof, including a hydrate thereof. For a review on suitable salts see Berge et al, J. Pharm. Sci, 1977, 66, 1-19.

Accordingly, a further aspect relates to a method for identifying one or more agents that modulate protein aggregation or protein folding comprising: providing a protein in a protein sample; performing the method according to the present disclosure on said protein sample in the presence and absence of one or more test agents that may modulate the aggregation of folding of the protein; and selecting one or more agents that modulate the aggregation or the folding of the protein, wherein a difference in the level of aggregation or folding in the presence of the test agents is indicative that the test agent modulates protein aggregation or folding.

A still further aspect relates to a method for monitoring protein aggregation over time comprising providing a protein in a protein sample; and performing the method according to the present disclosure on said protein at two or more different time points; wherein a difference between the results from the two or more different time points is indicative of a change in the aggregation of the protein over time.

A still further aspect relates to a method for screening of agents that modulate protein aggregation comprising providing the protein in a sample, adding a modulating agent, performing method set out in claims 1-20 and detecting presence or absence of change in protein conformation or stability.

A still further aspect relates to a method for screening for one or more agents that modulate protein aggregation comprising: providing a protein in a protein sample; performing the method according to the present disclosure on said protein sample in the presence and absence of one or more test agents that may modulate the aggregation of the protein; determining the amount of aggregation in the presence of the test agents, wherein a decrease in the amount of aggregation in the presence of the test agents is indicative that the test agent modulates protein aggregation.

Figure 10A:
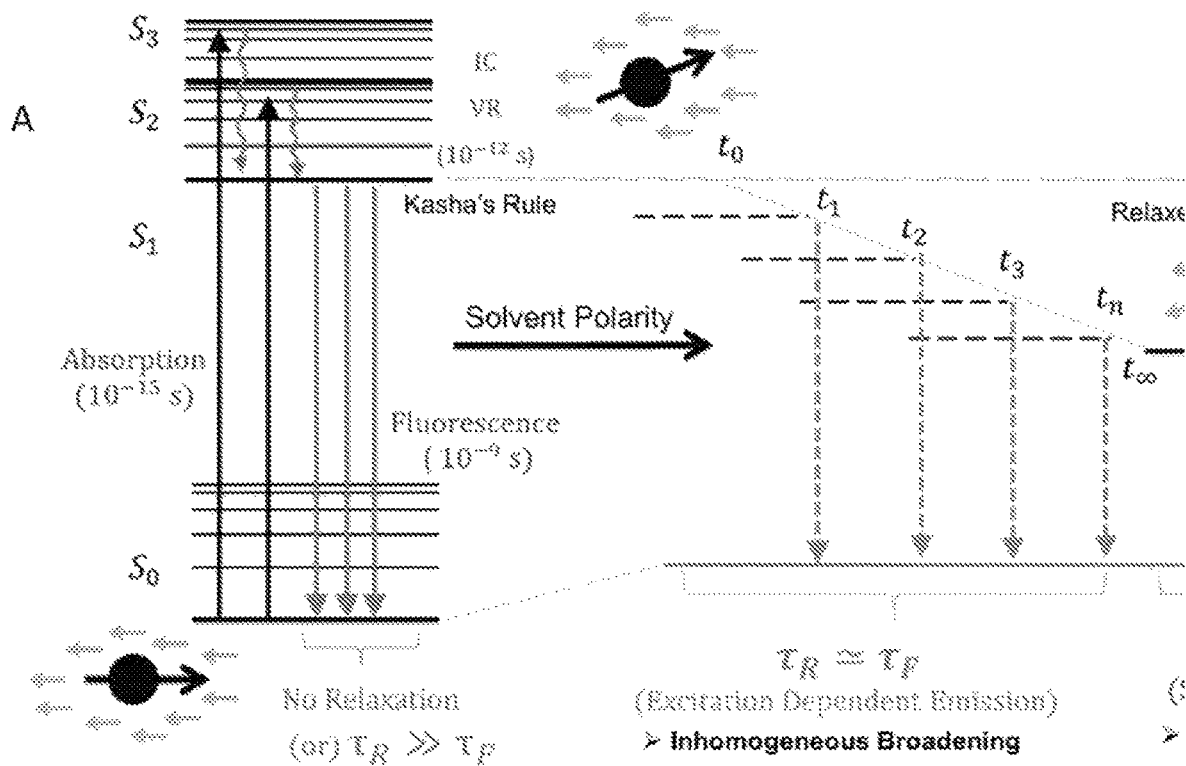
FIG. 10a illustrates schematically excitation and subsequent relaxation via fluorescent emission of a protein sample comprising a protein in a solvate including buffer ions.
Figure 10:
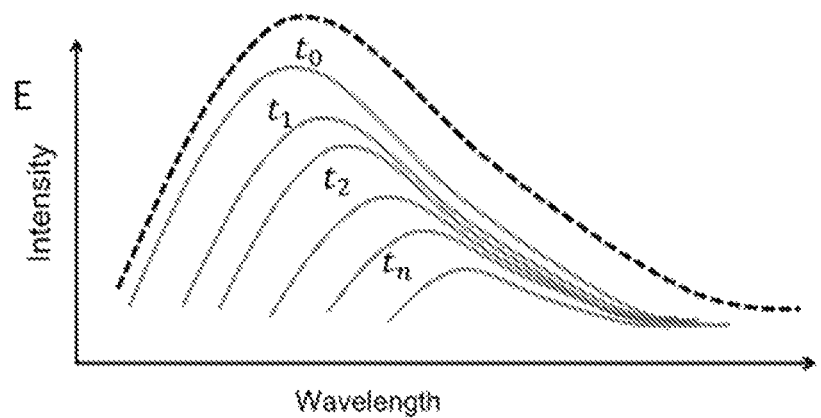
Figure 10:
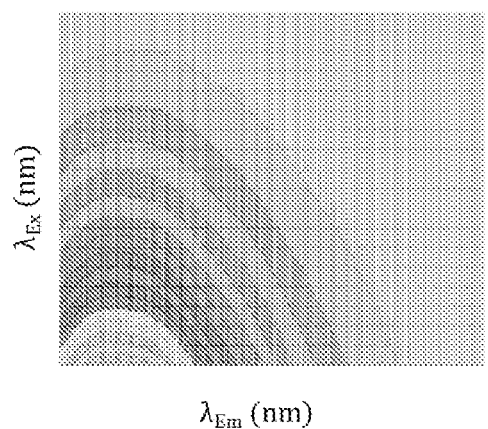

FIGS. 10a to 10c illustrate generally the REES effect observed in some proteins. Figure boa illustrates schematically excitation and subsequent relaxation via fluorescent emission of a protein sample comprising a protein in a solvate including buffer ions; FIG. 10b illustrates various emission spectra obtained from the protein sample of FIG. 10a; and FIG. 10c illustrates graphically a comparison of emission wavelength (x-axis) to excitation wavelength (y-axis) for the protein sample of FIG. 10a.

REES is a phenomenon where low energy excitation of a fluorophore leads to a red shift in the maximum of the emission intensity, $\Delta\lambda_{Em}^{max}$. This phenomenon may manifest where there are a range of discrete fluorophore solvation states and therefore potentially reflects the equilibrium of conformational states that are accessible to a protein [8,9].

The REES effect is governed by interactions between a flourophore and the surrounding solvent in the ground and excited states as shown in FIG. 10a. REES is observed as a result of the change in the dipole moment of the fluorophore following excitation and the speed at which solvent reorganisation occurs around the newly excited fluorophore [8,9]. In a fully solvated environment, the fluorescence lifetime ($\tau_F$) is much larger than the lifetime of environmental relaxation ($\tau_S$). In this case, the emission wavelength of the chromophore is independent of the excitation wavelength. When $\tau_F \ll \tau_S$, for example, in a rigid molecular environment such as some folded protein states, the intermolecular interactions between the fluorophore and its environment do not change and dipolar relaxation does not occur during fluorescence emission [10,11]. A consequence of this is that the fluorescence emission occurs at higher energy since photons are emitted from the excited state instead of a lower energy relaxed state. It is possible to select for individual solvation environments within an equilibrium by using low energy excitation (photoselection), for example, by using lower energy photons or longer wavelengths located at the red edge of the excitation spectrum [12]. Excitation at a lower energy selects for fluorophores in a solvent relaxed environment, which require less energy to become activated. Experimentally one observes a "red shift" in the emission maximum with respect to excitation wavelength.

There have been a few reports where emission arising from a single Trp residue gives a significant REES effect in the folded and molten globule like states [13], while the REES effect disappears or is rather reduced in unfolded states [14,15]. The REES effect is therefore a unique probe for proteins with a high degree of molecular flexibility resulting in an ensemble of solvent environments around the Trp probe. For proteins, such an ensemble may arise from a broad equilibrium of conformational states, such as in molten globule intermediates of highly flexible or dynamic proteins [14,16,17].

FIG. 11 illustrates schematically main component parts of apparatus configured to record fluorescence emission spectra and thus measure optical shift phenomena in some arrangements. In order to obtain REES data in relation to a protein, a protein sample is prepared. That protein sample typically comprises: the protein in an aqueous solution together with appropriately selected buffer ions. The protein sample is placed in a cell holder. The sample is illuminated with substantially single wavelength collimated light of a controlled, known, intensity. The sample absorbs the energy of the incident photons and, if fluorophores are present and in a physical position within the protein and the surrounding solution which allows it, the protein sample may exhibit a fluorescence emission spectrum. The emission spectrum of the protein sample may be appropriately detected by a detector and that emission spectrum passed to an analysis unit (CPU). The excitation of protein sample may be repeated at a plurality of excitation wavelengths, and associated fluorescence emission spectra detected and recorded. If the excitation wavelengths are chosen appropriately to match the expected fluorescence emission spectrum of the protein, it may be possible to analyse the various obtained emission spectra and obtain information relating to any edge shift effects including, for example, the REES effect exhibited by a protein sample.

One arrangement may provide an experimental method comprising: receiving a fluorescence emission spectrum generated by a protein sample at a first excitation wavelength, said protein sample being configured to exhibit fluorescence in dependence upon its conformational state; evaluating, from said fluorescence emission spectrum, an indication characteristic of a fluorescence response of said protein sample at said first excitation wavelength; repeating said receiving and evaluating steps in relation to a plurality of fluorescence emission spectra, each fluorescence spectrum generated by said protein sample at a different excitation wavelength to said first excitation wavelength; fitting a non-linear relationship between excitation wavelength and indication characteristic of fluorescence response of said protein sample, said non-linear relationship comprising a numerical model indicative of said conformational state of said protein sample, based upon correlation of said received excitation wavelengths and associated evaluated indications characteristic of said fluorescence response of said protein sample.

FIGS. 12a to 12C provide an overview of protein structure and analysis according to an arrangement which uses the REES effect as a specific reporter of mAb structure. FIG. 12a illustrates schematically a general structure of the fragment antigen-binding (Fab) region of a range of mAbs and such a protein may be tested in apparatus such as that shown and described in relation to FIG. 11.

FIG. 12b illustrates schematically example REES data for a mAb such as that shown in FIG. 12a. FIG. 12b shows an arrangement in which a Gaussian function is fitted to empirical data. FIG. 12C illustrates schematically one example plot of parameters extracted from a Gaussian function fitted to empirical data as in FIG. 12b for a series of different mAbs.

It can be seen from the plot of FIG. 12b that the empirical REES data appears to display a general curvature. To identify a numerical model that would best fit empirical REES data, some arrangements, such as the plot shown in FIG. 12b look at the change in the centre of spectral mass (CSM) of emission spectra and compare that across an extended range of excitation wavelengths. It will be appreciated that other parameters may be compared between spectra. For example, rather that the CSM, the peak emission wavelength or similar may be used.

In the example shown in FIG. 12b, the REES data obtained empirically can be represented by (fitted to) a Gaussian probability distribution of the form:

$$f(x) = CSM_0 + \frac{A\sqrt{2/\pi}}{w}\exp\left(-2\left(\frac{x-m}{w}\right)^2\right)$$ Equation 10.

Where A is the area, w is the full width at half-maximal (fwhm), m is the mid-point and $CSM_0$ is the y-intercept and $m=\lambda_{REES}^{max}$, where $\lambda_{REES}^{max}$ is the excitation wavelength that gives the largest change in the emission peak wavelength.

The empirically obtained REES data displays a good fit to Equation 10 and illustrate the low energy excitation at the red edge of the protein absorption spectrum. The fit of Equation 10 to the experimental data is good and captures expected relationships as described in more detail in relation to specific experiments set out in more detail below.

Some arrangements recognize that the magnitude of A extracted from fitting Equation 10 to a plot of excitation wavelength versus $\lambda_{Em}^{max}$, can be used as a qualitative comparator to assess changes in the extent of the observed REES phenomenon. The magnitude of $R_0$ should represent the minimum $\lambda_{Em}^{max}$ value, in the absence of the REES effect. This magnitude is commonly used to reflect the degree of solvent exposure of, for example, Trp residues in a protein sample and may, for example, be used as a metric of protein folded/unfolded states. Fitting experimental data to a suitable numerical model does not recapitulate the absorbance/excitation spectrum of a fluorophore yet may still provide a physically meaningful probe.

The experiments described in more detail below demonstrate that the REEs effect is sensitive to both unfolded, folded and stabilized protein states as reported by others and that a numerical model such as that set out in Equation 10 may accurately fit the empirically obtained data. Having established a quantitative model to compare REES data, the hypothesis that REES can be used to reflect changes in the equilibrium of protein conformational states was tested. In particular, the REES effect which occurred with both denatured and stabilized NEMO was monitored, and pressure-perturbation studies which systematically altered the equilibrium of conformational states were performed.

Based on analysis of native, denatured and stabilized protein, together with an understanding of theoretical basis of the REES effect, experiments were performed to demonstrate the magnitude of REES is sensitive to changes in the number of discrete equilibrium conformational states of a protein sample.

Non-denaturing pressure perturbation is an excellent tool for testing if REES is sensitive to changes in the number of discrete equilibrium conformational states of a protein sample, since changing pressure acts to perturb a pre-existing equilibrium of structural states characterized by different energy minima on the protein FEL [33]. Pressure has been used as a perturbation in a number of studies [34-36]. It will be understood that pressure, unlike temperature, does not alter the internal energy of the system, which might otherwise be a confounding factor for REES measurements. The observation of a significant pressure dependence on the REES effect itself is therefore be powerful evidence that REES is sensitive to the equilibrium of protein conformational states.

The pressure dependence data can be adequately fit to a simple, phenomenological model which implies a single transition between two states with changing hydrostatic pressure as used previously [23,38]. The key finding from the pressure data in the present context is that the REES effect itself is pressure-dependent with the magnitude of A increasing with pressure. Given that pressure acts to perturb the equilibrium of conformational states, this observation suggests that the magnitude of A extracted from Equation 10 is sensitive to this equilibrium.

Protein samples subjected to denaturation, pressure changes and macromolecular crowding (protein stabilization) measurements produce empirical data which suggests that the REES effect as modelled by Equation 10, is sensitive to changes in the equilibrium of conformational states, for example, by unfolding (chemical denaturation), stabilization/folding (macromolecular crowding) or direct perturbation (pressure). It appears that the magnitude of the REES effect can be used as a proxy for the protein free energy landscape (FEL), reflecting the distribution of discrete conformational sub-states.

Based on experimental observation, a conceptual framework for interpreting protein REES data using Equation 10, as shown in FIG. 5. As shown in FIG. 5, some aspects and embodiments recognise the information content that arises from, for example, the curvature of the REES data. Within this framework, the changing curvature of the REES data, reflected by the magnitude of A from in Equation 10, describes the progression to a larger or smaller number of discrete conformational states, a rugged or flat FEL, respectively. Furthermore, the intercept with the y-axis, $R_0$, can be used as an indicator of whether the protein sample tends towards a folded or unfolded state, in exactly the same way as might be expected from a traditional analysis of Trp emission in protein folding studies, but with the added benefit that the numerical model of Equation 10 as fitted to empirical data takes account of cases where the peak maximum of the emission band shifts with excitation wavelength. It is important to note that the terms "folded" and "unfolded" used on the context of the framework of FIG. 5 also encompass more minor conformational changes. So, for highly flexible and dynamic proteins, a blue shifted CSM may simply reflect a more compact conformational state (as suggested is the case from the crowding experiment results shown in FIG. 5), without requiring a large scale folding event.

Having outlined the general principles recognized by some aspects and embodiments, specific experiments performed in order to demonstrate those principles are set out in more detail in the Examples below:

EXAMPLES

Example 1: Details of the Experimental Approach Adopted to Demonstrate Links Between REES Effect and Protein Structure NF-κB essential modulator is the key regulatory element in the NF-κB signaling pathway, controlling much of the nervous and immune system [18]. NEMO regulates the activity of a kinase, IκB kinase-β (IKK-β), which has a diverse range of phosphorylation targets, for example, IκBα [19], huntingtin [20], and insulin receptor 1 (IRS-1) [21]. NEMO putatively ensures the specificity of IKK-β for IκBα, by facilitating the recruitment of IκBα to the kinase [19]. Subsequent proteosomal degradation of IκBα then allows the NF-κB complex to enter the nucleus and induce expression of pro-inflammatory and anti-apoptotic genes. Despite the importance of NEMO to normal human health and disease associated processes, remarkably little is known about the molecular mechanism of action of NEMO and, in particular how NEMO is able to show specificity to a very large number of interaction partners [22].

It has been observed that NEMO is a flexible protein that undergoes ligand specific conformational change, and have hypothesized that the non-ligand bound protein adopts a broad equilibrium of conformational states [23]. The emission of NEMO's single intrinsic Trp residue (W6) has been used as a spectroscopic reporter of ligand-induced NEMO conformational change [23].

The use of REES spectroscopy is described to inform on the structural and mechanistic determinants of NEMO-ligand binding. First, a new framework for the quantitative interpretation of steady-state REES data is described, validated by folding and pressure perturbation studies. This then allows us to use the REES data quantitatively for a series of NEMO-ligand bound states. A putative model for the molecular mechanism of NEMO's functional interactions, structure and how this connects to the NEMO free energy landscape and conformational change is developed.
NEMO W6 Shows a Significant REES Signal.

FIG. 1 shows the variation in emission spectrum (FIGS. 1A and 1B) and center of spectral mass (CSM) (FIG. 1B) of NEMO W6 versus excitation wavelength. Typically the magnitude of the steady-state REES phenomenon is reported as the simple difference in CSM or $\Delta\lambda_{Em}^{max}$. From FIG. 1, it is observed that a significant red shift in the emission spectra, with an increase in CSM of 17.7 nm and an increase in $\Delta\lambda_{Em}^{max}$ of 15 nm from $\lambda_{ex}$ 292-310 nm. Essentially the data are treated by the linear function:

$$CSM = R\lambda_{ex} + CSM_0 \qquad \text{Eq 1.}$$

Where R is the REES magnitude expressed as the change in CSM per nm of the excitation wavelength, $\lambda_{ex}$. In this model the y-intercept, $CSM_0$, does not have an obvious physical to meaning and is not typically reported. The solid grey line in FIG. 2B inset shows the fit of the NEMO REES data to Eq 1, giving R=0.96.

The extracted REES signal with NEMO W6 is large compared to other reported values and is even more significant given that NEMO W6 is already relatively solvent exposed. NEMO W6 is a class III Trp according to the Burstein classification [24]. Class III Trp residues are not typically thought to exhibit a significant REES effect [25] due to the very significant solvent exposure, thus giving rise to an essentially single solvated environment. However, denatured spectrin retains a significant REES signature, despite being largely solvent exposed [14]. These findings have been rationalized as reflecting a partially 'unfolded' state with residual structure, comparable to a molten globule state. It has been suggested that NEMO is a native molten globule [23] and so the present findings of a very significant REES effect for an already red-shifted tryptophan are consistent with previous results.

Physically, these findings suggest that NEMO adopts a very broad equilibrium of conformational states, where there are multiple discrete solvation environments for W6; this could arise both from a series of W6 micro-environments as well as from the stabilization of different Trp rotamers.

Pan et al have previously demonstrated that even solvent exposed Trp residues can display a broad range of $\Delta\lambda_{Em}^{max}$ values, arising from different Trp rotamers [26] and calculate a range 344-365 nm from molecular dynamics simulations for a range of cyclic peptides. This would seem consistent with the data that show a similar range of $\Delta\lambda_{Em}^{max}$ values. Further, Maglia et al find a significant REES effect in a single Trp variant of DD-carboxypeptidase attributable to at least three different Trp rotamers [27]. These rotamers may be stabilized through differing H-bonding to the Trp amide carbonyl [28]. As such it is difficult to directly separate the contribution of differing Trp rotamers and larger scale conformational heterogeneity of the peptide backbone to the REES signal. Below, the contribution of different Trp rotamers to the NEMO REES signal in detail is investigated.

Figure 8A:
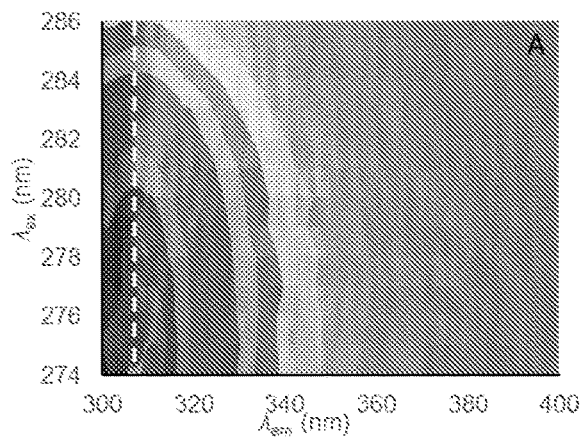
FIG. 8a is a contour plot showing the change in the structure of the emissions spectra with increasing $\lambda_{Ex}$. The dashed white line shows the change in the $\lambda_{Em}^{max}$ for each emission spectrum to aid the eye only.
Figure 8B:
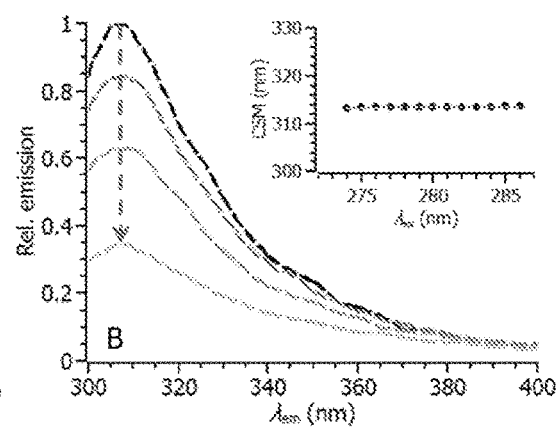
FIG. 8b illustrates graphically the relative change the intensity of W6 emission ($\lambda_{Em}^{max}$ shown as a dashed black line to aid the eye for increasing $\lambda_{Ex}$.

An artificial REES effect could arise if there is a significant convolution of the Trp signal with the background Tyr signal from NEMO. NEMO is excited from 292 nm upwards specifically so that there is essentially no Tyr emission relative to Trp emission. How a small Tyr signal would affect the REES data by monitoring the REES data for 10 μM Tyr in buffered solution and subtracting this from the NEMO REES data has been explored. These data are shown in FIG. 7. Accounting for the small Tyr signal arising from NEMO's intrinsic Tyr residues gives essentially no difference to the REES data. Further, the REES signal is monitored from a single Tyr containing fragment of Staphylococcus aureus complement evasion second immunoglobulin-binding protein Sbi domain III and IV that, like NEMO, is composed of a significant fraction of structurally disordered content [29]. These data are shown in FIG. 8. A significant REES signal arising from Tyr emission is not found as is expected because of the symmetrical nature of the Tyr ring system.

Together, these data demonstrate that the signal monitored, as expected, arises essentially entirely from NEMO's single intrinsic Trp.

Establishing a Quantitative Analysis of REES Data.

The fit of the REES data to Eq 1 is poor and does not account for the curvature in the data. This is the case for all reported steady-state REES data where a significant number of data point are collected. For REES data to be used in comparative studies, the reporting of R in Eq 1 will therefore be wildly inaccurate. To identify a numerical model that would best fit these data the change in the CSM of NEMO Trp emission is measured across an extended range of Trp absorption (shown in FIG. 2), incorporating the emission maximum of the Trp. The REES effect should be observable at the far red edge of the absorption spectrum, with little or no effect at the absorption maximum, since photoselection and hence REES will only occur under low energy excitation. From FIG. 2, this trend is apparent. That is, little or no REES effect is observed occurring at the maximum of the excitation spectrum but a significant REES effect at the red edge of the spectrum. The observed changes in CSM are dominated by NEMO's intrinsic Trp residue and not convolved of contributions from Tyr emission since it is shown above that, consistent with theory, Tyr emission does not give a measurable REES effect and does not convolute the REES data (FIG. 7). Indeed, emission from $\lambda_{Ex}$=292 nm is monitored, where there is essentially no emission attributable to tyrosine as shown in Figure S1.

The REES data in FIG. 2 can be best represented by a Gaussian probability distribution of the form:

$$f(x) = R_0 + \frac{A\sqrt{2/\pi}}{w}\exp\left(-2\left(\frac{x-m}{w}\right)^2\right) \qquad \text{Eq 2.}$$

Where A is the area, w is the full width at half-maximal (fwhm), m is the mid-point and $R_0$ is the y-intercept and $m=\lambda_{REES}^{max}$, where $\lambda_{REES}^{max}$ is the excitation wavelength that gives the largest change in the emission peak wavelength. The data in FIG. 2 are fit to Eq 2 and illustrate the low energy excitation at the red edge of the protein absorption spectrum. The fit of Eq 2 to the experimental data is excellent and captures the expected relationship described above.

Potentially, the magnitude of A extracted from fitting Eq 2 to a plot of excitation wavelength versus $\lambda_{Em}^{max}$, can be used as a qualitative comparator to assess changes in the extent of the REES phenomenon. The magnitude of $R_0$ should represent the minimum $\lambda_{Em}^{max}$ value, in the absence of the REES effect. This magnitude is commonly used to reflect the degree of solvent exposure of Trp residues and can be used as a metric of folded/unfolded states. The interpretation of these values is described in more detail below. This simple model clearly neglects a range of contributing factors such as the proportion of excited molecules, the small contribution from changing excitation energy at different excitation wavelengths, the number of discrete conformational states that are photo-selectable and the contribution from dipole rotation in the excited electronic state. However, Eq 2, unlike Eq 1, is based on a realistic physical rationale and provides a means to extract meaningful quantitative data from the full range of REES data. Other distribution functions can and have been used in relation to extracting information from spectral features, including Lorentz and log-normal distributions [30-31]. Ultimately it is not desired to try and accurately recapitulate the absorbance/excitation spectrum of the fluorophore but instead wish to have a physically meaningful probe beyond the arbitrary use of a simple linear function.

Validating REES as a Quantitative Probe of Molecular Heterogeneity.

Having established a quantitative model to compare REES data, the hypothesis that REES can be used to reflect changes in the equilibrium of protein conformational states is tested. To achieve this, the REES effect is monitored with both denatured and stabilized NEMO as well as pressure-perturbation studies that systematically alter the equilibrium of conformational states and the extracted parameters from fitting the data are given in Table 1.

TABLE 1

Results of fitting NEMO-ligand complex REES data to Eq 1 and Eq 2.

| | $A^a$ | $R_0$ (nm) | $R^a$ |
|---|---|---|---|
| Native, denatured, crowded | | | |
| $NEMO_{native}$ | 1 ± 0.1 | 363.2 ± 0.19 | 1 ± 0.13 |
| $NEMO_{denat}$ | 0.37 ± 0.4 | 375.0 ± 0.5 | 0.21 ± 0.01 |
| NEMO + Sbi (20 mg/ml) | 2.24 ± 0.51 | 360.5 ± 0.45 | 1.07 ± 0.12 |
| Binding partners | | | |
| NEMO + IκBα | 0.85 ± 0.04 | 364.1 ± 0.62 | 1.35 ± 0.1 |
| NEMO + NBD-Phe | 1.33 ± 0.31 | 363.0 ± 1.5 | 0.98 ± 0.1 |
| NEMO + $Ub_4$ | 0.77 ± 0.05 | 364.6 ± 0.77 | 1.06 ± 0.1 |
| NEMO + $Ub_{10}$ | 1.23 ± 0.0.1 | 362.8 ± 0.25 | 0.93 ± 0.11 |

$^a$Values are relative to the extracted value for NEMO alone.

Typically one does not expect to observe a significant REES effect with denatured protein since the peptide backbone will become fully solvent accessible. In this case, the solvent relaxation will be very rapid and no REES effect observed, effectively because there is one discrete solvation state (fully solvated). NEMO is incubated in 6M guanidine to denature the protein and the corresponding change in the center of spectral mass (CSM) versus $\lambda_{ex}$ is shown in FIG. 3. The use of CSM is favoured instead of the magnitude of $\Delta\lambda_{Em}^{max}$ as this metric gives a more robust REES signal and the magnitude of may be highly error prone. However the results using $\Delta\lambda_{Em}^{max}$ are essentially the same. A decrease and red-shift in Trp emission is typically grossly correlated with denaturation of proteins. From FIG. 3 the incubation with guanidine has significantly denatured NEMO, with a red-shift in CSM giving $R_0$=363.2±0.19 nm to $R_0$=375±0.5 for the native and denatured protein, respectively. Note that this is not the REES effect but reflective of the solvent exposure of NEMO W6 on denaturation. The denatured NEMO shows a dramatically reduced REES effect. Denatured NEMO shows only a 4 nm shift from $\lambda_{ex}$ 292 to 310 nm and fitting to Eq 1 gives R=0.22±0.02 and a relative decrease compared to native NEMO of R=0.23±0.1. Fitting to Eq 2 also gives a large decrease in the REES effect, A=0.37±0.4. The relative change in the REES effect is similar using either approach and this indicates strongly that a fitting approach using Eq 2 is robust.

Macromolecular crowding is a key feature of the intracellular milieu arising from the very high concentrations of other species in the cytosol. Crowding reduces the available solvent for other molecules in solution through the excluded volume effect, which effectively increase the concentration of, for example, protein and restricts the accessible conformational states through hard-core repulsions between the crowding agent and the protein. Macromolecular crowding can alter protein conformation, typically inducing folding and stabilization [32]. Crowding therefore potentially provides a means to explore the contrasting physical effect of denaturation on the REES effect, where the protein is more folded/stabilized. A protein has been used as the crowding agent, Sbi (reported above), instead of a synthetic crowding agent since protein is much more consistent with the intracellular environment. Sbi lacks any intrinsic Trp residues and does not give rise to a REES signal that would convolute the NEMO signal (FIG. 7). Incubating NEMO with a high concentration of Sbi (20 mg/ml) gives a dramatic change to the both the absolute Trp emission and also the REES effect as shown in FIG. 3. The emission is blue shifted ($R_0$=360.5±0.45 nm) compared to NEMO in the absence of Sbi ($R_0$=363.2±0.19) and more intense (~1.4 times larger emission), suggesting that the NEMO Trp is less solvent exposed and therefore that NEMO is more 'folded' in the crowded environment. Intriguingly, the REES effect is much larger in the crowded environment giving a relative increase in A of 2.24±0.51. These data therefore suggest that in a crowded environment, more similar to the intracellular milieu, NEMO has a more rugged FEL, able to explore a broader range of conformational states than observed in dilute buffered solution. This is consistent with findings from other studies, for example Dhar et al find the phosphoglycerate kinase shows an increase in conformational sampling in a crowded environment [32]. This is consistent with the putative molecular model of NEMO activity that is based on allosterically regulated NEMO conformational change. Below, the potential mechanistic role of an increased number of available conformational states with respect to ligand interactions is described.

Based on the native, denatured and stabilized protein analysis (FIG. 3) as well as the theoretical basis of the REES effect, the magnitude of REES should be sensitive to changes in the number of discrete equilibrium conformational states. Testing this is challenging since few experimental approaches give a direct window into the equilibrium of conformational states. Non-denaturing pressure perturbation is an excellent tool for this purpose since it acts to perturb a pre-existing equilibrium of structural states to characterized by different energy minima on the protein FEL [33] and has been used for this purpose in a number of studies [34-36]. Crucially pressure, unlike temperature, does not alter the internal energy of the system, which might otherwise be a confounding factor for REES measurements. The observation of a significant pressure dependence on the REES effect itself would therefore be powerful evidence that REES is sensitive to the equilibrium of protein conformational states.

Figures 9A, 9B:
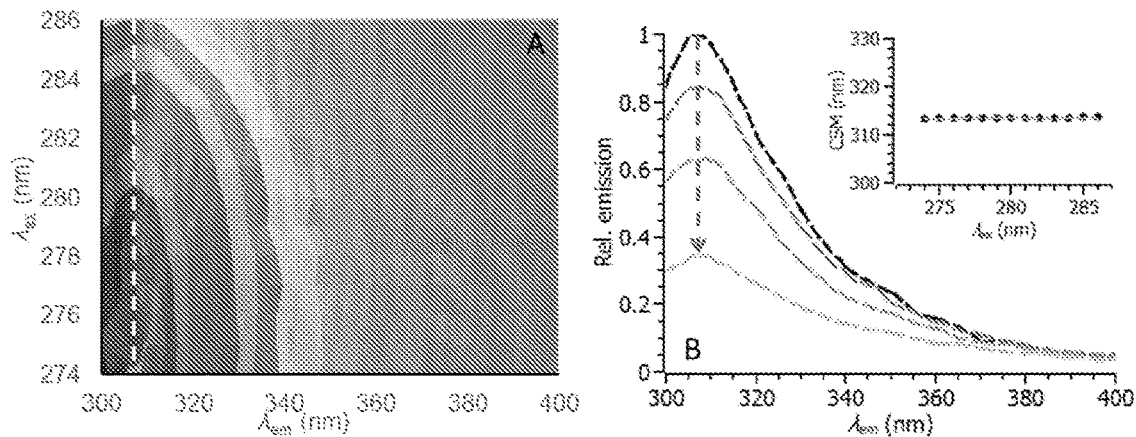
FIG. 9a illustrates schematically a comparison of low and high pressure REES data for NEMO W6 and free Trp.
FIG. 9b illustrates schematically difference data showing the change in the REES effect for both NEMO W6 and free Trp.

It has previously been found that increasing pressure causes a decrease in W6 emission, suggesting increased solvent exposure [23]. This finding is corroborated by a red shift in the W6 CSM with increasing pressure (FIG. 3A), giving an increase of 3.0 nm at $\lambda_{ex}$=292 nm. The CSM value is rather larger than reported for the denaturation study above (FIGS. 3A and 3B) and this is due to a different spectral window used to calculate the CSM for the pressure studies. This was necessary due to the optical setup of the pressure cell. The $\Delta\lambda_{Em}^{max}$ value of W6 at 1 bar is similar to that reported above, giving $\Delta\lambda_{Em}^{max}$=348 nm at 10° C., 1 bar and $\lambda_{ex}$=295 nm. Increasing pressure leads to a large CSM at higher $\lambda_{ex}$ values, giving an increase of 8.9 nm at $\lambda_{ex}$=310 nm from 1 to 2000 bar. These data suggest that the REES effect itself is pressure-dependent. Fitting the REES data to Eq 4 gives the pressure dependence of A, shown in FIG. 4D as the change in the fraction of A across the pressure range. No REES effect is observed with free Trp in buffered solution at any pressure (FIG. 9) and the changes observed are protein specific. The pressure dependence data can be adequately fit to a simple, phenomenological model that implies a single transition between two states with changing hydrostatic pressure as used previously [23,38]:

$$\frac{A_i}{\Sigma A}(p, T) = \frac{K(p, T)}{1 + K(p, T)} = \frac{\exp(\ln K_0 - \Delta V_A p/R_p T)}{1 + \exp(\ln K_0 - \Delta V_A p/R_p T)} \quad \text{Eq 3.}$$

Where $R_p$=83.13 cm3 mol$^{-1}$ bar K$^{-1}$ when the pressure, p, is measured in bar, $K_0$ is the equilibrium constant for the change in the relative population of the ith conformational state represented by the magnitude of A from Eq 4, extrapolated to 0 bar and $\Delta V_A$ is the apparent difference in the volume associated with this equilibrium transition.

Fitting the data in FIG. 4 to Eq 3 gives a negative activation volume $\Delta V$=-24.7±4.7 cm3 mol$^{-1}$. $\Delta V$ for W6 emission has been measured and it is found (as shown here) that the emission decreases across the pressure range giving $\Delta V$=0.81=0.03 cm3 mol$^{-1}$[23]. The difference in sign is simply attributable to relative change in direction of the specific to signal. What is important is that the magnitude of $\Delta V$ is much larger for the REES effect compared to W6 emission. Indeed, this magnitude of pressure dependence is more consistent with global metrics of NEMO conformational change previously measured using the pressure dependence of 8-anilino naphthalene sulfonate (ANS) emission [23]. The REES signal may therefore be reflective of the broader equilibrium of NEMO conformational states at sites distal to W6. That is, these two values are not necessarily comparable, reflecting different aspects of the W6 molecular environment. The key finding from the pressure data in the present context is that the REES effect itself is pressure-dependent with the magnitude of A increasing with pressure. Given that pressure acts to perturb the equilibrium of conformational states, this observation suggests that the magnitude of A extracted from Eq 2 is exquisitely sensitive to this equilibrium.

The findings from denaturation, pressure and macromolecular crowding measurements suggest that the REES effect as modelled by Eq 2, is sensitive to changes in the equilibrium of conformational states, e.g. by unfolding (chemical denaturation), stabilization/folding (macromolecular crowding) or direct perturbation (pressure). As such, it is suggested that the magnitude of the REES effect can be used as a proxy for the protein free energy landscape (FEL), reflecting the distribution of discrete conformational sub-states. Based on the observations a conceptual framework for interpreting protein REES data using Eq 2, shown in FIG. 5 is developed. The interpretation of the present data moves beyond current applications by explicitly recognizing the information content that arises from the curvature of the REES data. Within this framework, the changing curvature of the REES data, reflected by the magnitude of A from Eq 2, describes the progression to a larger or smaller number of discrete conformational states, a rugged or flat FEL, respectively. In addition, the intercept with the y-axis, $R_0$, describes whether the protein tends towards a folded or unfolded state, in exactly the same way as per the normal analysis of Trp emission in protein folding studies, but with the added benefit that it takes account of cases where the peak maximum of the emission band shifts with excitation wavelength. It is important to note that the terms folded and unfolded encompass more minor conformational changes also. So for highly flexible and dynamic proteins a blue shifted CSM may simply reflect a more compact conformational state (as suggested is the case from the crowding experiment shown in FIG. 2), without requiring a large scale folding event.

It is important to recognize that REES data from protein Trp residues will be convolved of the signal arising from different Trp rotamers [26]. However, the observations suggest that at least for NEMO, the REES signal is not significantly convolved of a signal from Trp rotamers. That is, the pressure dependence of the REES gives a very large activation volume (~24.7±4.7 cm3 mol$^{-1}$), much larger than based on Trp emission alone (~1.6±0.4 cm$^3$ mol$^{-1}$) and more consistent with measurements that reflect global NEMO conformational change [23]. Moreover, it is demonstrated below that ligand binding at sites that are not located near the Trp residue significantly alter the REES signal and this is powerful evidence that the NEMO REES signal is dominated by the proteins global structural ensemble.

Novel Insight from REES on the Nature of NEMO Allostery and Ligand Induced Conformational Change.

Having established that the REES effect, specifically the use of Eq 2, can be used as a proxy for the protein free energy landscape, how the NEMO REES signal varies upon ligand binding is considered. These data should give more direct insight into the mechanism of ligand induced conformational change and the relationship to the protein FEL. The REES data for NEMO ligand bound states are shown in FIGS. 6A and 6B with the solid lines representing the fit to Eq 2. The resulting extracted values of A from Eq 2 are given in Table 1 and also as an inset bar chart in FIG. 6. For clarity, the relative change in R and A compared to NEMO alone is reported, extracted from Eq 1 and 2, respectively.

FIG. 6A shows NEMO alone and bound to either a peptide mimic of IκBα or IKK-β. The IKKβ peptide (termed the NEMO binding domain, NBD) contains two Trp residues and so is not suitable for the present study as the signal from the peptide would confound the analysis of the single NEMO Trp. Instead these Trp residues are replaced with a conservative amino acid, Phe, and called NBD-Phe. it is found that this modified peptide binds to NEMO, giving a decrease in W6 emission of ~50%. From Table 1 and FIG. 5A there is a significant difference in the magnitude of A depending on the ligand bound form of NEMO. That is, A decreases significantly on IκBα peptide binding (A=0.85±0.04) but increases significantly on NBD-Phe binding (A=1.33±0.3). If the ligand binding data shown in FIG. 5A is fitted to the simple linear function described by Eq 1 a different trend is found. That is, from Eq 3, IκBα peptide binding increases the relative magnitude of the REES effect (R=1.35±0.1) and IKK-β peptide binding gives essentially no change in the relative magnitude of the REES effect (R=0.98±0.1). From FIG. 6A it is apparent that the REES data are not equivalent with NEMO bound to NBD-Phe and NEMO alone as suggested by the fit to Eq 1. Instead the major difference to is in the curvature of the data and this is captured by the use of Eq 2. Based on the findings from the pressure data discussed above, it is suggested that these data reflect a decrease in the number of discrete conformational states on IκBα binding, but an increase in the number of discrete conformational states on IKK-β binding. This oppositional relationship is supported by the previous NEMO-ligand binding studies monitoring the change in ANS emission [23], which suggest the exposure of hydrophobic residues on IKK binding and the burying of hydrophobic residues on IκBα.

NEMO comprises a specific domain that non-covalently binds poly-ubiquitin. It has previously been found that binding of long chain-length 'free' M1-linked poly-ubiquitin chains to NEMO allosterically regulates ligand affinity and potentially cellular localization based on evidence from stopped-flow and liposome binding assays [23]. Poly-ubiquitin is found as a range of chain-lengths in the cell and evidence has previously been provided from ANS binding studies that NEMO undergoes different conformational change depending on the chain-length of non-covalently bound poly-ubiquitin [23]. The REES effect on NEMO W6 is explored in the presence of both short (4-mer; $Ub_4$) and long (10-mer; $Ub_{10}$) poly-ubiquitin chains, as shown in FIG. 6B. From the resulting values of A, given in Table 1, $Ub_4$ binding gives a decrease in A (A=0.77±0.05), but $Ub_{10}$ gives an increase (A=1.23±0.1). A simple linear fit to Eq 1 suggests no difference in REES with either chain length giving A of ~1 within error (Table 1), despite obvious differences in the curvature of the data sets. The absolute magnitude of the REES difference is small. A broad trend is observed that potentially suggests that longer chain lengths induce a broader range of accessible NEMO conformational states.

Based on the most current NEMO structural model the poly-ubiquitin binding site is not located near the native Trp residue [23,37]. That a significant change in the REES effect is observed for this Trp is consistent with the notion that poly-ubiquitin binding alters NEMO conformation or dynamics in an allosteric fashion. The trend for a decrease in REES with shorter poly-ubiquitin chain lengths and an increase at longer chain-lengths mirrors the binding of ANS that was reported previously [23]. That is, a decrease in ANS emission is observed (suggesting burying of hydrophobic residues) at short chain lengths and an increase (suggesting exposure of hydrophobic residues) at longer chain lengths. Combined, these data suggest that shorter poly-ubiquitin chain lengths may drive compaction (burying of hydrophobics and a reduction in the equilibrium of conformational states) and longer chain lengths may drive expansion (exposure of hydrophobics and an increased equilibrium of conformational states) of NEMO. The REES data further suggest that these changes are not large scale folding or unfolding to events since the $R_0$ values (Table 1) are essentially the same. Based on these data it is believed that, without being bound by any particular theory, the allosteric regulation of NEMO by poly-ubiquitin occurs by modulating the available equilibrium of conformational states, rather than gross structural change.

There is a great deal of contemporary interest in the relationship between the equilibrium of native protein conformational states and how this equilibrium changes upon ligand binding [38-41]. Based on insight from the current data, it is suggested that NEMO predominately utilizes a conformational selection model of ligand binding. That is, NEMO adopts a range of equilibrated conformational states represented by discrete energetic minima on the protein FEL. Ligand binding occurs at one of these pre-existing conformers, shifting the equilibrium towards the ligand bound population.

For example as shown above, IκBα binding gives a significant reduction in the number of NEMO conformers, implying a less rugged FEL for the binary complex. However, this model could be extended to suggest that ligand binding may also induce new conformational states, as well as expanding the number of discrete states within the population (a more rugged FEL) as with NBD and $Ub_{10}$. A potential mechanistic rationale for this finding is that the new conformational space allows new molecular interactions, not accessible to the non-ligand bound protein alone. Indeed, $Ub_{10}$ enhances the affinity of NEMO for IKK-β and IκBα and promotes liposome association [23]. Based on the present data it is believed that, without being bound by any particular theory, this allosteric effect is achieved by exposing new high affinity binding sites or additional binding determinants for these species.

A recent study by Bagnéris et al [37] have modeled the NEMO structure as a parallel coiled coil and have provided experimental evidence for this structural model from PELDOR (pulsed electron electron double resonance studies). It has previously been found from far-UV CD studies that NEMO is composed primarily of α-helical (~50%) and random coil (~40%) and the present data suggest that the NEMO structure occupies an equilibrium of conformational states. These data can be resolved by a model where NEMO is in a dynamic equilibrium between well folded (coiled coil) and locally unfolded (random coil) states. This dynamic equilibrium can then be differently stabilized on ligand binding, with IκBα giving rise to an increased proportion of folded content and IKK-β/poly-ubiquitin giving more unstructured content. This model would then be consistent with the PELDOR data, ANS binding studies and the present REES data.

Methods

Protein Expression and Purification.

Full length human NEMO was expressed and purified essentially as described previously [23]. Purified protein was dialysed extensively into a buffer comprising 50 mM Tris-Cl pH 8.0, 50 mM NaCl and 5 mM DTT. All measurements were made in this buffer unless otherwise stated. IKK-β and IκBα peptides were commercially synthesised by Genscript, having a purity of >98% and are of the sequence TALDFSFLQTE and DDRHDSGLDSMKD, respectively. The IKK-β peptide was modified such that the two native Trp residues were replaced with Phe residues. M1-linked poly-ubiquitin was purchased from Viva Bioscience. Staphylococcus aureus immune modulator protein fragment Sbi-III-IV K173A was expressed and purified essentially as described previously [44]. Protein concentration used was between 1 and 5 µM. Peptide concentrations were 1 mM and poly-ubiquitin concentrations were 1 µM.

Red Edge Excitation and High-Pressure Measurements

All fluorescence measurements were performed using a Perkin Elmer LS50B Luminescence Spectrometer (Perkin Elmer, Waltham, Mass., USA) connected to a circulating water bath for temperature regulation (±1° C.). Samples were incubated for 5 minutes at the given conditions prior to recording measurements. Measurements were performed at 10° C., unless otherwise stated. Excitation and emission slit widths were 5 nm except for pressure experiments where they were 10 nm. The larger slit width was required due to the optical setup of the pressure cell to ensure a low signal-to-noise for the W6 emission signal. For NEMO red edge excitation scans, tryptophan emission was monitored from 315 to 550 nm. The excitation wavelength was subsequently increased in 1 nm steps for a total of 19 scans. For red edge excitation scans, tyrosine emission was monitored from 294 to 400 nm, with the excitation wavelength set at 274 nm. Similarly, the excitation wavelength was subsequently increased in mm steps for a total of 19 scans. The corresponding buffer or buffer and ligand control was subtracted from the spectra for each experimental condition. Specifically, for the crowding experiment with Sbi, the emission is subtracted from the Sbi so the signal is not convolved of Sbi Tyr emission in any way.

An ISS high-pressure cell (ISS, Champaign, UL, USA), fitted with a custom fiber optic mounting to the fluorimeter and connected to a circulating water bath for temperature regulation was used to record all high-pressure measurements. For NEMO high-pressure red edge excitation measurements, tryptophan emission was monitored between 325-450 nm.

The center of spectral mass (CSM) was calculated using the following equation:

$$CSM = \frac{\Sigma(f_i \times \lambda_{Em})}{\Sigma(f_i)} \qquad Eq\ 4$$

Where $f_i$ is the measured fluorescence intensity and $\lambda_{em}$ is the emission wavelength. The importance of using a consistent wavelength range when reporting CSM data is stressed, as the magnitude will be dependent on the wavelength range chosen. As such, the CSM across the emission range 325-450 nm or 335-450 nm is reported for pressure experiments.

Example 2: Revealing Protein Conformation and Stability Using a Quantitative Understanding of Biomolecular Edge Shift Using a panel of therapeutic mAbs it is demonstrated that the sensitivity of this approach can be used to discern between structurally identical antibodies, quantify native and unfolded states, detect the earliest stage formation of soluble aggregates and most importantly, can be used to predict thermodynamic stability. This tool will find immediate use in making stable biopharmaceutical formulations and could significantly cut the cost of the drug development process. It is demonstrated that not only is the approach able to follow the progression towards unfolded and aggregated states independently it is also able to be used in a predicative capacity to infer thermodynamic stability. The findings demonstrate that the present disclosure provides a simple, powerful tool to monitor protein conformational state and opens the door to this approach being adopted widely as part of the commercial quality assurance process, formulation of biopharmaceuticals and use in academic labs.

QUBES Reports on a Proteins Dynamic Profile.

Figures 13A, 13B, 13C, 13D:
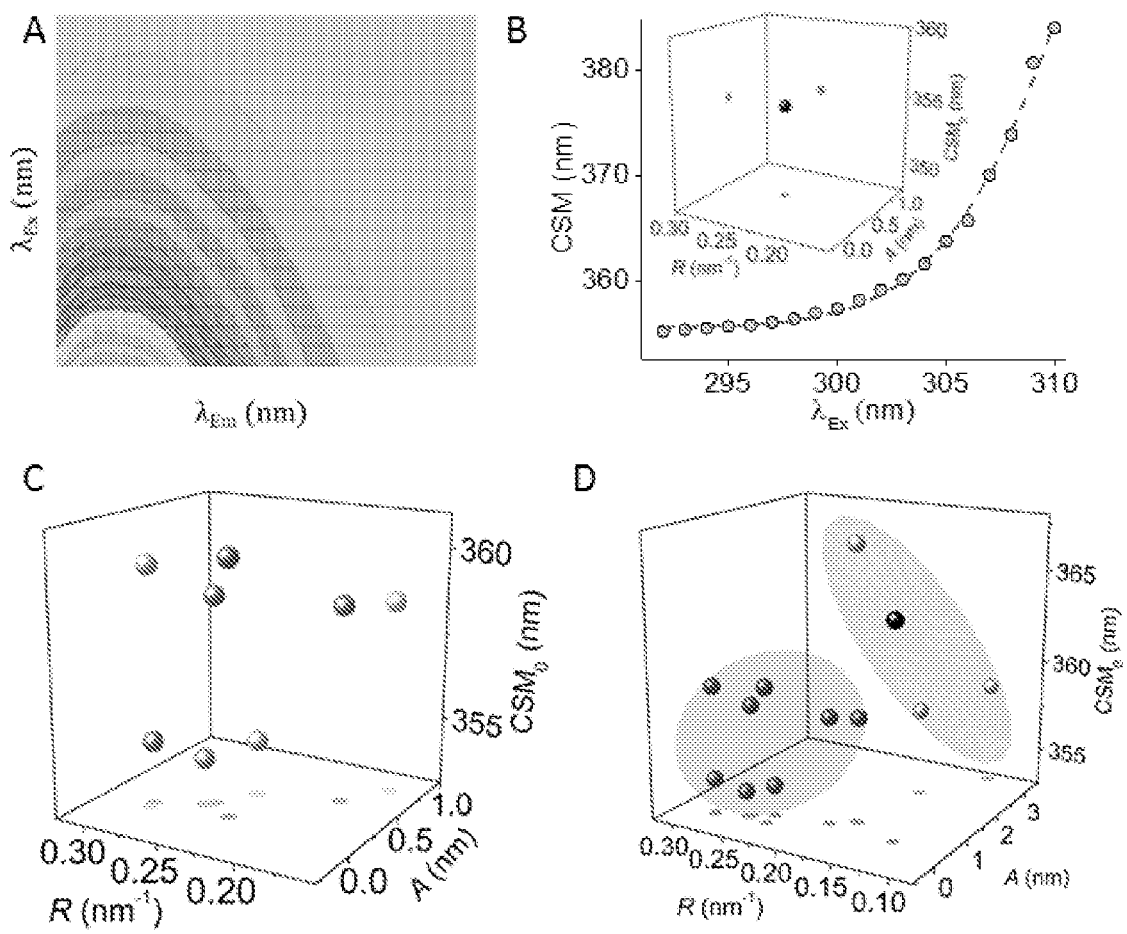
FIG. 13A to D illustrate QUBES values for a range of mAbs when fit to an exponential function.

The edge-shift effects for a range of mAbs, have been monitored and are shown in FIG. 13 A-C. First, the combined excitation and emission spectrum is monitored for each mAb giving a high information content fluorescence data set (FIG. 13A). The intensity and peak position of the emission incorporates information on (i) the number of Trp residues in the sample (ii) the degree of solvent exposure of the Trp residues[24] including arising from different rotamers (iii) energy transfer to the peptide backbone,[42] homotransfer to other Trp residues[43] and (iv) photoselection of discrete solvation environments at low energy excitation.[44] Contributions from Tyr emission are essentially negligible over the excitation range used.[24] From these data (FIG. 13A) one can extract the variation in the emission spectra with excitation wavelength as either the change in the emission peak position ($\lambda_{max}$) or as the change in the centre of spectral mass (CSM). The use of CSM is preferred as it does not require model fitting to accurately extract the emission peak maximum and incorporates information on the whole dataset. FIG. 13B shows an example of the resulting plot of CSM versus excitation wavelength for an example mAb. These data show marked curvature, similar to reports with proteins containing single Trp residues.[24] Simple linear fitting of these data is clearly inadequate to capture the full information content contained in the data set. A Gaussian distribution has been fitted to these data to capture the information contained in the curvature of the edge-shift data.[24] This approach tends to lead to relatively large error values since the model contains a large number of variable parameters. A simpler exponential function is fitted, $$CSM = CSM_0 + Ae^{R\Delta\lambda \cdot Ex} \qquad \text{Eq 1.}$$

Where $CSM_0$ is the CSM value independent of the excitation wavelength, $\lambda_{Ex}$, determined by the amplitude, A, of an exponential with a curvature determined by R. Fitting with this function instead of a Gaussian or other probability distribution dramatically improves the speed of data processing due to the lower dimensionality of the model but still retains the key aspects of the previous model, namely quantification of the magnitude of the fluorescence edge-shift. The plot of the resulting parameters yields a single three-dimensional data point (FIG. 13B, inset; the QUBES value), which is a direct quantification of the extremely complex spectral fingerprint shown in FIG. 13A.

QUBES values for a range of therapeutic mAbs are measured from different classes including, chimeric (ximab), humanised (zumab) and human (lumab) in the same buffer system. The humanised mAbs are shown in FIG. 31C and all of the examples in FIG. 13D. There is a very significant difference in the QUBES value for each of the mAbs studied and between classes of mAb. That is, the humanised mAbs exhibit an entirely separate clustering of QUBES values to humanised mAbs. The individual QUBES values are extremely reproducible both for individual replicates of the same sample and also batch-to-batch variation, with a typical standard deviation of ~20% for A, ~10% for R and <1% for $CSM_0$. As such, the differences in FIG. 13C are bone fide and do not represent the absolute variance across the samples as a whole.

Figures 20, 21:
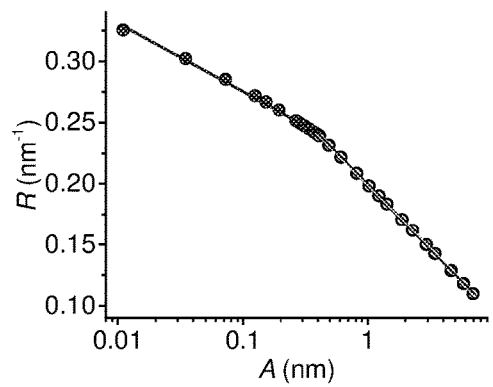

The separation of the QUBES values (FIG. 13D) is extremely surprising given the very high sequence conservation of the mAbs and the overall structural similarity of the Fab region where one finds the highest variability. Nine of the twelve examples studied are of the IgG1 isotype except Pembrolizumab, Vedolizumab and Natalizumab, which are IgG4, differing only by three residues in the hinge region and retaining the same inter-heavy chain disulphide bonds. For the same class of mAb (chimeric, humanised or human) the three-dimensional structures can be considered to be essentially identical. Indeed, the far-UV circular dichroism spectrum and dynamic light scattering (DLS) profile of these full length mAbs is highly similar if not identical (see below) as expected for proteins with high sequence similarity and similar overall structures particularly in the percentage of secondary structure content. The Fab region (FIG. 18) contains the most sequence variability and there are some small differences in the number and/or position of Trp residues for some of the mAbs in the Fab region (FIGS. 18 and 18B and Table of FIG. 21). However, these differences (number of residues and solvent accessible surface area) do not correlate show a correlation with the extracted QUBES values (FIGS. 18C and 18D). It was previously suggested that the curvature in the REES effect captures information on the equilibrium of conformational states accessible to the FEL, which can be thought of as the proteins relative rigidity/flexibility and it is believed this is at least part of the origin of the detection sensitivity of quantitating the curvature in REES data.

QUBES Detects and Quantitates Protein Unfolding and Aggregation.

Figures 14A, 14B, 14C, 14D:
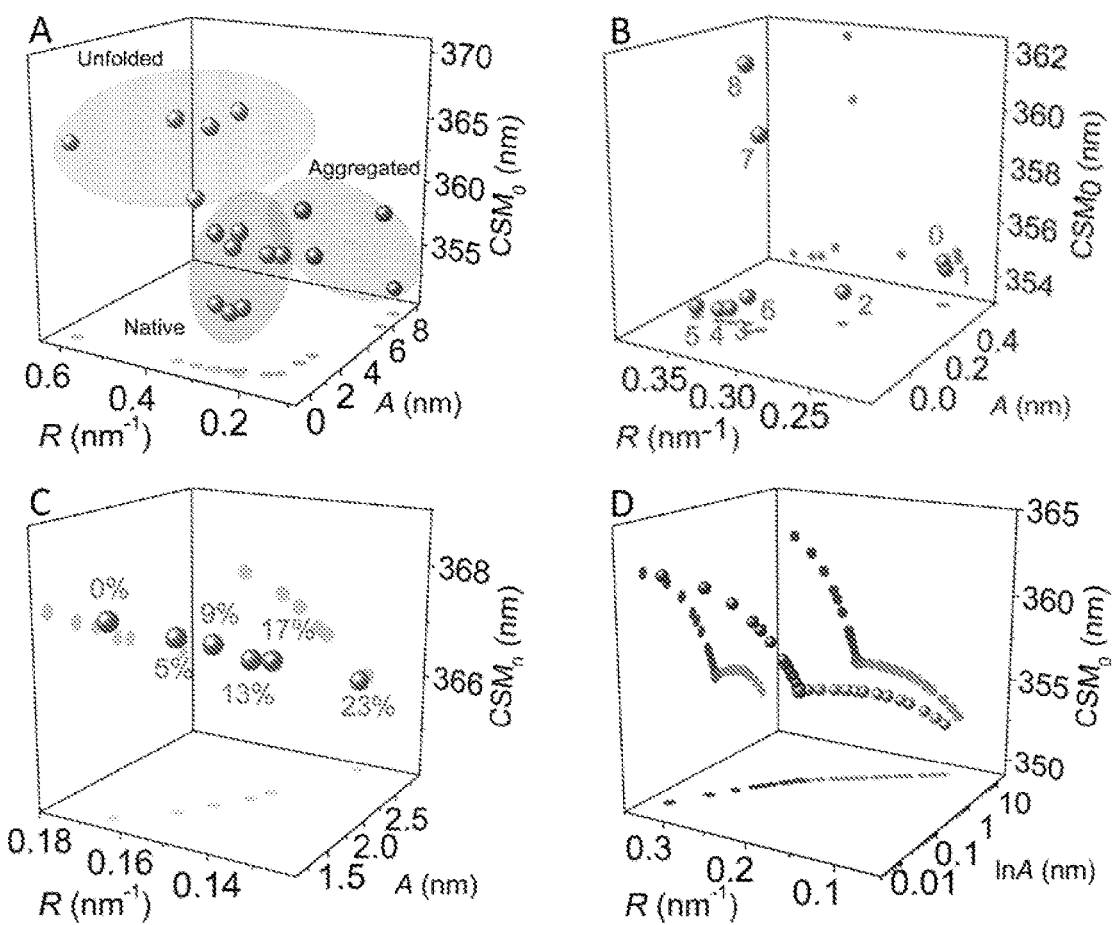
FIG. 14A to D show how QUBES values can be used to reflect and differentiate between mAb unfolding and early stage aggregate formation.

Changes in protein structure are accompanied by a change in the equilibrium of conformational states. It has been previously found with a model system, a 'hub' protein (described above), that by quantitating the curvature in REES data it is possible to capture information on unfolded states and ligand induced conformational change. It was explored whether the sensitive detection of differences in REES data could be useful for detecting subtle changes in protein structure in mAbs. It is tested whether the QUBES data can be used to identify unfolding and aggregation of the mAbs since these are key issues facing the development of biopharmaceuticals. FIG. 14A shows the QUBES data for mAbs incubated in 8M urea and thermally denatured, respectively. Incubation with urea will cause the mAbs to partially unfold (retaining the native disulphide linkages), but also prevent aggregate formation, whereas thermal denaturation, particularly for the mAbs studied, directly drives aggregate formation. The formation of soluble aggregates is monitored in the thermally denatured mAbs by dynamic light scattering (DLS), shown in FIG. 19.

FIG. 14A shows that the unfolded (urea denatured) mAbs cluster to higher $CSM_0$ and R values, but smaller A values. These data reflect a flatter REES effect of a smaller total magnitude based on a simple linear fit. Based on the findings from model protein studies of the REES effect,[24] these data may reflect more solvent exposed Trp residues (indicated by the higher $CSM_0$) and a decrease in the range of conformational states available to the protein. These notions are in-line with the range of proteins that have been observed to have a decreased REES effect upon unfolding, which reflects the transition towards a restricted equilibrium of conformational states characterised by a fully unfolded protein.[45, 15, 13] Conversely, treating the gross trends in the whole data set (FIG. 14A), it is found that thermally denatured mAbs cluster to elevated A values, but similar R and $CSM_0$ values (these changes are explored in more depth below). Based on the corresponding DLS data (FIG. 18), the increase in the magnitude of A would therefore seem to predominately reflect the formation of soluble aggregates. The QUBES value is not only able to discern native and denatured protein but also to separate proteins that are unfolded from those that are aggregated.

The observed variance in the QUBES values for the denatured mAbs (FIG. 14A) may reflect the differing extent of unfolding or aggregation for each of the samples and the specific nature of the unfolded or aggregated states. This is confirmed by monitoring the sequential unfolding of Tocilizumab and aggregation of Rituximab shown in FIGS. 14B and 14C, respectively. The unfolding of Tocilizumab proceeds with an initial shift in the QUBES value to a larger R and smaller A value (FIG. 14B). This finding is consistent with other studies that report a smaller overall edge-shift for unfolded versus native protein since the protein is tending towards a single conformational state; unfolded.[45, 25, 13] Only at higher concentrations of urea (7M) is a significant increase in the $CSM_0$ value observed. An increase in the CSM might indicate more solvent exposed Trp residues indicative of protein unfolding.[24] The change in CSM or related metrics such as the emission ration 350:330 nm or the emission maximum ($\lambda_{max}$) are commonly used to assess protein unfolding since it potentially reflects changes in protein tertiary structure. The data therefore illustrate that these metrics ignore early stage changes to protein structure that are not captured by simple steady-state fluorescence emission measurements.

In order to monitor the gradient of effect for mAb aggregation a sample of aggregated (soluble aggregates only) Rituximab is titrated into a non-aggregated sample and the resulting QUBES values are shown in FIG. 14C. An essentially linear trend in the QUBES value is observed with respect to an increasing proportion of soluble aggregate, manifesting as a decrease in the magnitude of R and $CSM_0$ and an increase in A. The decreasing $CSM_0$ value may reflect Trp residues becoming more buried in the aggregated protein. The QUBES values show a significant shift (outside of the error of the measured values) at concentrations as low as 5% soluble aggregate.

Further evidence for this trend is provided by calculating the expected change in the data by numerically modelling an increasing fraction of unfolded and aggregated mAb shown in FIG. 14D and FIG. 20. This approach has the advantage that there is no question of re-folding or disaggregation. The modelled values are generated by increasing the fractional contribution of the unfolded/aggregated spectrum to the native protein spectrum and performing the QUBES analysis on the resulting spectra. Similar to the trend in FIG. 14C, that there is an essentially linear variation in the QUBES value for increasing fractions of unfolded/aggregated protein, where the value of A is plotted on a logarithmic scale as shown in FIG. 20. This means that a calibration curve can easily be produced to estimate the fraction of unfolded or aggregate material in a sample simply by measuring QUBES values for native and full denatured protein.

Figures 15A, 15B, 15C, 15D, 15E:
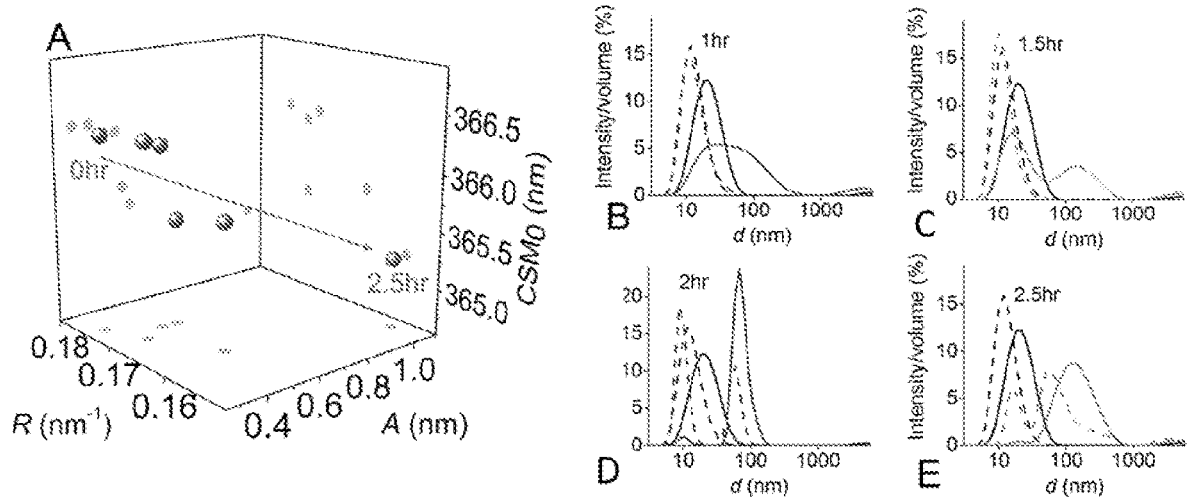
FIG. 15A to E compares the sensitivity of QUBES values to DLS profiles.

The presence of protein aggregates is one of the key criteria in biopharmaceutical quality assurance and control and is typically monitored using light scattering approaches such as DLS. To this end a time course of thermal aggregation of Nivolumab is monitored by both QUBES and DLS and the data are shown in FIGS. 15A and 15B-E, respectively. An increase in A and a decrease in R and $CSM_0$ is observed, correlated with increasing formation of soluble aggregates. Both QUBES and DLS data show a significant shift at 1 hr incubation (FIG. 15B). The QUBES values show a significant shift prior to a change in the volume data from DLS (FIGS. 15B and 15C) and even where there are only subtle shifts in the intensity data (FIG. 15D). Intensity DLS profiles are vastly more sensitive than volume DLS profiles, but volume data are typically preferred as they can potentially be quantitative and often suffer from false positives. Given that the QUBES value shows a significant shift prior to a change in the volume of DLS profiles, the QUBES value can be used to quantify the percentage of soluble aggregates with detection that is at least as sensitive and accurate as DLS.

In summary, the QUBES approach should be extremely sensitive to protein secondary, tertiary and quaternary structure change. This may be because it captures information on subtle changes to the proteins equilibrium of conformational states. The data corroborate this, demonstrating that the QUBES value is sensitive to, and can quantitate, increasing fractions of unfolded or aggregated species at very high sensitivity.

Using QUBES as a Predictive Tool and for Formulation of Therapeutics.

Given the extreme sensitivity of the QUBES approach to separately detecting and quantifying both unfolding and soluble aggregate formation, the approach may find best utility in the prediction and formulation of stable biopharmaceutical preparations. The quantification of the curvature in REES data might reflect information on protein flexibility (see below). Increased protein flexibility is typically correlated with decreased thermodynamic stability because there is a smaller energetic barrier of unfolding as evidenced from a range of mesophile versus thermophile enzyme studies.[46] Those mAbs predicted to be relatively rigid (small A and high R value) e.g. Pertuzumab may be more stable than those predicted to be relatively flexible (high A and small R value) e.g. Nivolumab. The thermal stability of three mAbs with QUBES values has been explored suggesting increasing flexibility (Pertuzumab, Vedolizumab and Nivolumab), by monitoring the formation of soluble aggregates at the same temperature for each mAb, shown in FIG. 16A. Based on the QUBES values and the corresponding DLS profiles (FIG. 16B) there is a trend for a more significant fraction of soluble aggregate present for Nivolumab compared to Vedolizumab compared to Pertuzumab. These data therefore confirm that the QUBES value can be used in predictive manner to infer the relative thermodynamic stability of a sample. The predictive power is only appropriate for the same sample, since each protein will exhibit a specific QUBES signature. In the present case, the mAbs have three dimensional structures that are essentially identical and so the comparison between them is valid.

The power of the QUBES approach for formulation of stable biopharmaceutical preparations has been determined. To that end the temperature induced unfolding and aggregation of Pembrolizumab has been monitored both in the presence and absence of a known adjuvant (glucose) and the resulting QUBES values and DLS profiles are shown in FIGS. 16C and 16D, respectively. Incubation of Pembrolizumab at 37° C. for 5 days induces significant formation of soluble aggregates. However, based on detection with the QUBES approach, glucose provides significant protection from aggregate formation with a lower percentage of soluble aggregate formation as assessed by both the QUBES value and DLS profiles (FIGS. 15D and 15E). Indeed, the QUBES value for the glucose containing sample shifts to a small A and high R value, which is indicative of a more stable protein (described above). A similar result is found for Vedolizumab as shown in FIG. 20 using even shorter incubation times. No post-translational modification of the mAbs (glycation) is observed based on a fluorescence reporter system[47] and so the effect is due to stabilisation of the mAbs and not an artefact arising from glycation.

CONCLUSIONS

By experimentally monitoring a large number of mAbs a robust schematic for the interpretation of the QUBES value as shown in FIG. 17 is provided. Using QUBES it is possible to accurately detect, separate and quantify both protein unfolding and early stage formation of soluble aggregates as well as a predictor of sample stability. QUBES is better than approaches that are routinely used as present. The QUBES analysis has the advantages that: (i) data acquisition and analysis is rapid (<5 mins) so can be used as part of large scale screening; (ii) it can be used with any protein which includes one or more Trp residues (most proteins), (iii) using proteins of any size and in nearly any solvation/buffer environment; (iv) the measurements can be high-throughput (96 well plate); (v) samples are not consumed, (vi) the approach requires only a low sample concentration and (vii) a single QUBES value captures a complete set of information on the proteins conformation. The approach is designed to be used in a comparative fashion and is most robust and finds best utility when examining e.g. variants of buffer conditions for the same protein. Given the significant advantages of QUBES over existing approaches, QUBES may find immediate utility in both the formulation and quality assurance of biopharmaceuticals, but also in academic labs more generally that seek to understand the role of protein dynamics in protein function. For example, there is presently intense scrutiny of the role of early stage protein aggregation in amyloidogenic proteins involved in neurodegenerative disease. Given the very high sensitivity of QUBES to detecting and quantifying protein soluble protein aggregates, the use of the approach will deliver novel insight into the formation of these potentially toxic species.

Methods

QUBES Data Collection.

All fluorescence measurements were performed using a Perkin Elmer LS50B Luminescence Spectrometer (Perkin Elmer, Waltham, Mass., USA) connected to a circulating water bath for temperature regulation (±1° C.). Samples were incubated for 5 minutes at the given conditions prior to recording measurements. Measurements were performed at 10° C., unless otherwise stated. Excitation and emission slit widths were 5 nm. Tryptophan emission was monitored from 325 to 500 nm. The excitation wavelength was subsequently increased in 1 nm steps for a total of 19 scans. 3 sets of individual scans were averaged. The corresponding buffer control was subtracted from the spectra for each experimental condition and this also removes the Raman water peak. The centre of spectral mass (CSM) was calculated using the following equation:

$$CSM = \frac{\Sigma(f_i \times \lambda_{Em})}{\Sigma(f_i)} \qquad \text{Eq 4}$$

Where $f_i$ is the measured fluorescence intensity and $\Delta_{em}$ is the emission wavelength. The importance of using a consistent wavelength range when reporting CSM data is described, as the magnitude will be dependent on the wavelength range chosen. The QUBES data are extracted by fitting the CSM versus $\lambda_{Ex}$ data as described in the manuscript. Data fitting and plotting was performed using OriginPro 2016 (Microcal).

Antibody Samples, Unfolding and Aggregation.

Antibodies were provided by Bath ASU and were either extensively dialysed (for urea denaturation experiments) or diluted into Tris-Cl buffered saline pH 8. All buffer components were of a spectroscopic grade. Antibody denaturation was achieved by extensive dialysis into a buffered solution of 8M urea or 0M urea as a control. Antibody aggregation was achieved through incubation at elevated temperatures and monitored by DLS.

FIG. 13 shows QUBES values for a range of mAbs that are correlated with differences in molecular flexibility. A, The QUBES value are extracted from a combined excitation-emission spectrum for protein Trp residues. B, The CSM versus excitation wavelength (grey data) is fit to Eq 1, to give a single data point governed by 3 parameters and this is called the QUBES value (shown in inset). C, QUBES values for a series of zumab examples; Pembrolizumab (green), Vedolizumab (blue), Pertuzumab (orange), Natalizumab (yellow), Bevacizumab (Indigo), Trastuzumab (red), Trastuzumab emtansine (light blue) and Tocilizumab (light green). D, The QUBES values reflect the difference in intra-molecular flexibility between mAbs of the same class showing zumabs coloured red, ximabs (Rituximab, Infliximab and Cetuximab) coloured blue and Nivolumab coloured black. The corresponding coloured planes represent the 30% confidence interval for the data sets and are to aid the eye.

FIG. 14. A, The QUBES value can be used to accurately reflect and differentiate between mAb unfolding and early stage aggregate formation. QUBES values for zumab shown in FIG. 13C (red), incubated in 8M urea (red) and thermally aggregated (purple). B, Tocilizumab QUBES data under increasing concentrations of urea (red numbers in are [urea] (M)) titration of Urea, C, the sensitivity of QUBES value to aggregation. The data show the titration of fully aggregated Rituximab into native protein with the data points sequentially from left to right corresponding to 0, 5, 9, 13, 17 and 23% aggregate. D, Numerical modelling of increasing fractions of unfolded (blue) and aggregated (brown) Tocilizumab based on fully unfolded (8M urea) and fully solubley aggregated sample QUBES values.

FIG. 15. A-E, Comparing the sensitivity of the QUBES value to DLS profiles. A, QUBES values for Nivolumab incubated at 65° C. with values recorded every 30 minutes. B-E, Corresponding DLS profiles showing both % intensity (solid lines) and % volume (dashed lines) readings compared to the fresh sample (black). No change in the DLS profiles was observed at 0.5 hrs.

FIG. 16. QUBES predicts thermodynamic stability. A, A depiction of the protein FEL illustrating the link between protein flexibility and the equilibrium of conformational states and the change in the QUBES value parameters. Increasingly unstable proteins, characterised by a broad equilibrium of conformational states, located higher up the FEL, exhibit increased A and $CSM_0$ values and decreased R values. B, QUBES values for 3 example mAbs predicted to have different thermodynamic stabilities. C, Thermally driven aggregation of the mAbs in panel B for 3 hours [Pertuzumab (red) and Vedolizumab (green)] and [Nivolumab (blue)] at 65° C. and a concentration of 0.5 mg/ml. Arrows indicate the transition from 0 hrs to 3 hours incubation. D, Thermally driven aggregation (5 days at 37° C.) of Pemrolizumab (black) in the presence (orange) and absence of 60 mM glucose, respectively. Arrows indicate the transition from the beginning to the end of the incubation. E, Corresponding DLS profiles from panel D. Black solid line represents a non-aggregated mAb.

FIG. 17. Summary of the detection capability of QUBES. The change in position of QUBES data separately reflects unfolding and aggregation as well as (de)stabilisation. The stability of the sample is a reflection of the changing molecular flexbility (increasing rigidity providing increasing stability).

FIG. 18 A PyMol representation of an overlay of all RosettaAntibody homology models. FIG. 18A, The conserved tryptophans are displayed in stick representation and are highlighted in orange. It can be seen that the conserved 47th residues on the $V_H$ chain (boxed) have been modelled at two different orientations. The other conserved tryptophan residues are modelled in the same orientation. FIG. 18B, shows the same image, but with all (conserved and un-conserved) residues highlighted in blue. It is clear that the additional un-conserved tryptophan residues are located in a similar area of the molecule, and appear to be closer to the edge of the molecule (less-buried). Within each mAb Fab studied, there are between 4-7 tryptophan residues. The majority of these residues are conserved in the same position within the framework regions of the chains and are presented in the same orientation. FIG. 18 B demonstrates that it is the un-conserved tryptophans that are less buried, reflected in elevated SASA values. Some of these residues are found in the CDR loops. FIG. 18C shows the correlation of the QUBES value with Trp solvent accessible surface area (SASA) in the Fab region. FIG. 18D shows the correlation of the QUBES value with the number of Trp residues in the Fab region.

FIG. 19 shows the DLS profiles for thermally aggregated mAbs shown in FIG. 14A.

FIG. 20 shows the correlation between the changing magnitude of the QUBES value represented by the parameters A and R with increasing unfolded content (blue) and aggregated content (brown).

FIG. 21 shows a supporting information table showing a summary of calculated parameters for mAb Fab regions.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents. Indeed, various modifications of the described modes for carrying out the invention which are obvious to those skilled in physical chemistry, protein chemistry, protein biology and biochemistry or related fields are intended to be within the scope of the following claims. All publications mentioned in the above specification are herein incorporated by reference.

REFERENCES

1. Uversky V N (2013) A decade and a half of protein intrinsic disorder: Biology still waits for physics. Protein Sci. 22, 693-724.
2. Tsai C J, Buyong M, Sham Y Y, Kumar S & Nussinov R (2001) Structured disorder and conformational selection. Proteins Struct. Funct. Genet. 44, 418-427.
3. Sobolewska-Stawiarz A, Leferink N G, Fisher K, Heyes D J, Hay S, Rigby S E & Scrutton N S (2014) Energy landscapes and catalysis in nitric-oxide synthase. J. Biol. Chem. 289, 11725-11738.
4. Laursen T, Singha A, Rantzau N, Tutkus M, Borch J, Hedegård P, Stamou D, Møller B L & Hatzakis N S (2014) Single molecule activity measurements of cytochrome P450 oxidoreductase reveal the existence of two discrete functional states. ACS Chem. Biol. 9, 630-634.
5. Ferreon A C M, Ferreon J C, Wright P E & Deniz A (2013) Modulation of allostery by protein intrinsic disorder. Nature 498, 390-394.
6. Ruotolo B T, Giles K, Campuzano I, Sandercock A M, Bateman R H & Robinson C V (2005) Evidence for macromolecular protein rings in the absence of bulk water. Science. 310, 1658-61.
7. Sugase K, Dyson H J, Wright P E (2007) Mechanism of coupled folding and binding of an intrinsically disordered protein. Nature 447, 1021-1025.
8. Chattopadhyay A & Haldar S (2014) Dynamic insight into protein structure utilizing red edge excitation shift. Acc. Chem. Res. 47, 12-19.
9. Demchenko A P, (2002) The red-edge effects: 30 years of exploration. Luminescence 17, 19-42.
10. Weber G & Shinitzky M (1970) Failure of Energy Transfer between Identical Aromatic Molecules on Excitation at the Long Wave Edge of the Absorption Spectrum. Proc. Natl. Acad. Sci. U.S.A 65, 823-830.
11. Galley W C & Purkey R M (1970) Role of heterogeneity of the solvation site in electronic spectra in solution. Proc. Natl. Acad. Sci. U.S.A 67, 1116-1121.
12. Chattopadhyay A & Mukherjee S (1999) Red Edge Excitation Shift of a Deeply Embedded Membrane Probe: Implications in Water Penetration in the Bilayer. J. Phys. Chem. B 103, 8180-8185.
13. Kelkar D, Chaudhuri A, Haldar S & Chattopadhyay A (2010) Exploring tryptophan dynamics in acid-induced molten globule state of bovine alpha-lactalbumin: a wavelength-selective fluorescence approach. Eur. Biophys. J. 39, 1453-1463
14. Mitra M, Chaudhuri A & Patra M (2015) Organization and Dynamics of Tryptophan Residues in Brain Spectrin: Novel Insight into Conformational Flexibility. J Fluoresc. 25, 707-17.
15. Chattopadhyay A, Rawat S S, Kelkar D, Ray S & Chakrabarti A (2003) Organization and dynamics of tryptophan residues in erythroid spectrin: novel structural features of denatured spectrin revealed by the wavelength-selective fluorescence approach. Protein Sci. 12, 2389-2403.
16. Jain N, Bhasne K, Hemaswasthi M & Mukhopadhyay S (2013 Structural and dynamical insights into the membrane-bound α-synuclein. PLoS One 8, e83752.
17. Rawat S S, Kelkar D & Chattopadhyay A (2004) Monitoring gramicidin conformations in membranes: a fluorescence approach. Biophys. J. 87, 831-843.
18. Gilmore T D (2006) Introduction to NF-kappaB: players, pathways, perspectives. Oncogene 25, 6680-6684.
19. Schröfelbauer B, Polley S, Behar M, Ghosh G & Hoffmann A (2012) NEMO Ensures Signaling Specificity of the Pleiotropic IKKβ by Directing Its Kinase Activity toward IκBα. Mol. Cell 47, 111-121.
20. Thompson, L. M. Aiken C T, Kaltenbach L S, Agrawal N, Illes K, Khoshnan A, Martinez-Vincente M, Arrasate M, O'Rourke J G, Khashwji H, Lukacsovich T, Zhu Y Z, Lau A L, Massey A, Hayden M R, Zeitlin S O, Finkbeiner S, Green K N, LaFerla F M, Bates G, Huang L, Patterson P H, Lo D C, Cuervo A M, Marsh J L & Steffan J S (2009) IKK phosphorylates Huntingtin and targets it for degradation by the proteasome and lysosome. J. Cell Biol. 187, 1083-1099
21. Nakamori Y, Emoto M, Fukuda N, Taguchi A, Okuya S, Tajiri M, Miyagishi M, Taira K, Wada Y & Tanizawa Y (2006) Myosin motor Myoic and its receptor NEMO/IKK-γ promote TNF-α-induced serine307 phosphorylation of IRS-1. J. Cell Biol. 173, 665-671.
22. Fenner B J, Scannell M & Prehn J H M (2010) Expanding the substantial interactome of NEMO using protein microarrays. PLoS One 5, e8799.
23. Catici D A M, Home J E, Cooper G E & Pudney C R (2015) Poly-ubiquitin drives the molecular interactions of NF-κB essential modulator by allosteric regulation. J. Biol. Chem. 290, 14130-9.
24. Reshetnyak Y K, Koshevnik Y & Burstein E A (2001) Decomposition of Protein Tryptophan Fluorescence Spectra into Log-Normal Components. III. Correlation between Fluorescence and Microenvironment Parameters of Individual Tryptophan Residues. 81, 1735-58.
25. Demchenko A P (1988) Red-edge-excitation fluorescence spectroscopy of single-tryptophan proteins. Eur. Biophys. J. 16, 121-129.
26. Pan C P, Callis P R & Barkley M D (2006) Dependence of tryptophan emission wavelength on conformation in cyclic hexapeptides. J. Phys. Chem. B 110, 7009-7016.
27. Maglia G, Jonckheer A, De Maeyer M, Frère J-M & Engelborghs Y (2008) An unusual red-edge excitation and time-dependent Stokes shift in the single tryptophan mutant protein DD-carboxypeptidase from Streptomyces: the role of dynamics and tryptophan rotamers. Protein Sci. 17, 352-361.

28. Xu J, Chen J, Toptygin D, Tcherkasskaya O, Callis P, King J, Brand L & Knutson J R (2009) Femtosecond fluorescence spectra of tryptophan in human gamma-crystallin mutants: Site-dependent ultrafast quenching. J. Am. Chem. Soc. 131, 16751-16757.

29. Upadhyay A, Burman J D, Clark E A, Leung E, Isenman D E, van den Elsen J M & Bagby S (2008) Structure-function analysis of the C 3 binding region of *Staphylococcus aureus* immune subversion protein Sbi. J. Biol. Chem. 283, 22113-22120.

30. Djikanović D, Kalauzi A, Jeremić M, Mićić M & Radotić K. (2007) Deconvolution of fluorescence spectra: Contribution to the structural analysis of complex molecules. Colloids Surfaces B Biointerfaces 54, 188-192.

31. Caarls W, Soledad Celej M, Demchenko A P & Jovin T M. (2010) Characterization of coupled ground state and excited state equilibria by fluorescence spectral deconvolution. J. Fluoresc. 20, 181-190.

32. Dhar A, Samiotakis A, Ebbinghaus S, Nienhaus L, Homouz D, Gruebele M & Cheung M S (2010) Structure, function, and folding of phosphoglycerate kinase are strongly perturbed by macromolecular crowding. Proc Natl Acad Sci USA. 107, 17586-91.

33. Akasaka K (2006) Probing conformational fluctuation of proteins by pressure perturbation. Chem. Rev. 106, 1814-1835

34 Pudney C R, Hay S, Levy C, Pang J, Sutcliffe M J, Leys D & Scrutton N S (2009) Evidence to support the hypothesis that promoting vibrations enhance the rate of an enzyme catalyzed H-tunneling reaction. J. Am. Chem. Soc. 131, 17072-17073.

35. Hay S, Pudney C R, Sutcliffe M J & Scrutton N S (2010) Probing active site geometry using high pressure and secondary isotope effects in an enzyme-catalysed 'deep' H-tunnelling reaction. J. Phys. Org. Chem. 23, 696-701.

36. Collins M D, Kim C U & Gruner S M (2011) High-pressure protein crystallography and NMR to explore protein conformations. Annu. Rev. Biophys. 40, 81-98.

37. Bagnéris C, Rogala K B, Baratchian M, Zamfir V, Kunze M B, Dagless S, Pirker K F, Collins M K, Hall B A, Barrett T E & Kay C W (2015) Probing the Solution Structure of IκB Kinase (IKK) Subunit γ and its Interaction with Kaposi's Sarcoma Associated Herpes Virus Flice Interacting Protein and IKK Subunit β by EPR Spectroscopy. J. Biol. Chem. 290, 16539-49

38. Vogt A D & Di Cera E (2013) Conformational selection is a dominant mechanism of ligand binding. Biochemistry 52, 5723-5729.

39. Okazaki K-I & Takada S (2008) Dynamic energy landscape view of coupled binding and protein conformational change: induced-fit versus population-shift mechanisms. Proc. Natl. Acad. Sci. U.S.A 105, 11182-11187.

40. Wlodarski T & Zagrovic B (2009) Conformational selection and induced fit mechanism underlie specificity in noncovalent interactions with ubiquitin. Proc. Natl. Acad. Sci. U.S.A 106, 19346-19351

41. Nussinov R, Ma B & Tsai C J (2014) Multiple conformational selection and induced fit events take place in allosteric propagation. Biophys. Chem. 186, 22-30.

42. Muiño, P. L., and Callis, P. R. (2009) Solvent effects on the fluorescence quenching of tryptophan by amides via electron transfer. Experimental and computational studies. *J. Phys. Chem. B*. 113, 2572-2577.

43. Moens, P. D. J., Helms, M. K., and Jameson, D. M. (2004) Detection of tryptophan to tryptophan energy transfer in proteins. *Protein J.* 23, 79-83.

44. Azumi, T., Itoh, K., and Shiraishi, H. (1976) Shift of emission band upon the excitation at the long wavelength absorption edge. III. Temperature dependence of the shift and correlation with the time dependent spectral shift. *J. Chem. Phys.* 65, 2550-2555.

45. Catici, D. A. M., Amos, H. E., Yang, Y., van den Elsen, J. M. H., and Pudney, C. R. (2016) The red edge excitation shift phenomenon can be used to unmask protein structural ensembles: implications for NEMO-ubiquitin interactions. *FEBS J.* 283, 2272-2284.

46. Daniel, R. M., Danson, M. J., Eisenthal, R., Lee, C. K., and Peterson, M. E. (2008) The effect of temperature on enzyme activity: New insights and their implications. Extremophiles 12, 51-59

47. Morais, M. P. P., Fossey, James, T. D. and Van Den Else, J. M. H. (2012) Analysis of protein glycation using phenylboronate acrymalide gel elctrophoresis. Methods Mol. Biol. 869, 93-109

The invention claimed is:

1. A method comprising:
   receiving a fluorescence emission spectrum generated by a protein sample at a first excitation wavelength, the protein sample being configured to exhibit fluorescence in dependence upon its conformational state;
   evaluating, from the fluorescence emission spectrum, an indication characteristic of a fluorescence response of the protein sample at the first excitation wavelength;
   repeating the receiving and evaluating steps in relation to a plurality of fluorescence emission spectra, each fluorescence spectrum generated by the protein sample at a different excitation wavelength to the first excitation wavelength;
   generating a non-linear relationship between excitation wavelength and indication characteristic of fluorescence response of the protein sample, the non-linear relationship comprising an indication of at least one characteristic of the conformational state of the protein sample, based upon correlation of The received excitation wavelengths and associated evaluated indications characteristic of the fluorescence response of the protein sample; and
   determining a characterisation of the conformational state of the protein sample based on curvature of the generated non-linear relationship.

2. The method according to claim 1, wherein the indication of at least one characteristic of tithe conformational state of the protein sample comprises an indication of a number of discrete conformational states of a protein in the protein sample.

3. The method according to claim 1, wherein the indication of at least one characteristic of the conformational state of the protein sample comprises an indication of a free energy landscape of a protein in the protein sample.

4. The method according to claim 1, wherein the indication of at least one characteristic of the conformational state of the protein sample comprises an indication of a magnitude of curvature of the relationship between excitation wavelength and indication characteristic of fluorescence response of the protein sample.

5. The method according to claim 4, wherein the indication of the characteristic of fluorescence response which is determined to be independent over a range of excitation wavelength, and the indication of a magnitude of curvature of the relationship between excitation wavelength and indication characteristic of fluorescence response of the protein sample, together comprise a 2-dimensional fingerprint characteristic of the protein sample.

6. The method according to claim 1, wherein the indication of at least one characteristic of the conformational state of the protein sample comprises an indication of a relative folded or unfolded nature of the conformational state of a protein in the protein sample.

7. The method according to claim 1, wherein the indication of at least one characteristic of the conformational state of the protein sample comprises an indication of crowding of a protein in the protein sample.

8. The method according to claim 1, wherein the indication of at least one characteristic of the conformational state of the protein sample comprises an indication of physical compactness of a protein in the protein sample.

9. The method according to claim 1, wherein the indication of at least one characteristic of the conformational state of the protein sample comprises an indication of stability of a protein in the protein sample.

10. The method according to claim 1, wherein the indication of at least one characteristic of the conformational state of the protein sample comprises an indication of aggregation of a protein in the protein sample.

11. The method according to claim 1, wherein the indication of at least one characteristic of the conformational state of the protein sample comprises an indication of the indication characteristic of fluorescence response which is determined to be independent over a range of excitation wavelength.

12. The method according to claim 1, wherein the non-linear relationship between excitation wavelength and indication characteristic of fluorescence response of the protein sample comprises an exponential function or a symmetric or asymmetric exponential probability function.

13. The method according to claim 1, wherein the non-linear relationship between excitation wavelength and indication characteristic of fluorescence response of the protein sample comprises:
a Gaussian probability distribution of the form:

$$f(x) = R_0 + \frac{A\sqrt{2/\pi}}{w}\exp\left(-2\left(\frac{x-m}{w}\right)^2\right)$$

where A is the area, w is the full width at half-maximal (fwhm), m is the mid-point and Ro is the y-intercept and m=$\lambda_{REES}^{max}$, where $\lambda_{REES}^{max}$ is the excitation wavelength that gives the largest change in the fluorescence emission peak wavelength.

14. The method according to claim 1, wherein the protein sample comprises: a protein, solvent and buffer, and the indication of at least one characteristic of the conformational state comprises an indication of the conformational state of the protein in the solvent and buffer.

15. The method according to claim 1, comprising generating the indication of at least one characteristic of the conformational state of the protein sample for a plurality of different protein samples.

16. The method according to claim 1, comprising: comparing said indication of at least one characteristic of said conformational state of said protein sample with a previously generated indication of at least one characteristic of said conformational state of an identical protein sample.

17. The method according to claim 1, comprising comparing the indication of at least one characteristic of the conformational state of the protein sample, with an indication of at least one characteristic of the conformational state of a protein sample comprising the same protein having one or more different: concentration, solvent or buffer.

18. A non-transitory computer readable medium storing instructions that, when executed by at least one processor, cause a computer system to:
receive a fluorescence emission spectrum generated by a protein sample at a first excitation wavelength, the protein sample being configured to exhibit fluorescence in dependence upon its conformational state;
evaluate, from the fluorescence emission spectrum, an indication characteristic of a fluorescence response of the protein sample at the first excitation wavelength;
repeat the receiving and evaluating steps in relation to a plurality of fluorescence emission spectra, each fluorescence spectrum generated by the protein sample at a different excitation wavelength to the first excitation wavelength;
generate a non-linear relationship between excitation wavelength and indication characteristic of fluorescence response of the protein sample, the non-linear relationship comprising an indication of at least one characteristic of the conformational state of the protein sample, based upon correlation of the excitation wavelengths and associated evaluated indications characteristic of the fluorescence response of the protein sample; and
determine a characterisation of the conformational state of the protein sample based on curvature of the generated non-linear relationship.

19. A protein structure analysis unit apparatus comprising:
a sample holder to receive a protein sample;
a controllable light source operable to excite the protein sample;
a detector to detect a fluorescence emission spectrum produced by the protein sample;
a control unit in communication with the controllable light source and detector, the control unit comprising a protein structure analysis system comprising:
at least one processor; and
a non-transitory computer readable storage medium storing instructions that, when executed by the at least one processor, cause the protein structure analysis system to:
receive a fluorescence emission spectrum generated by the protein sample at a first excitation wavelength, the protein sample being configured to exhibit fluorescence in dependence upon its conformational state;
to evaluate, from the fluorescence emission spectrum, an indication characteristic of a fluorescence response of the protein sample at the first excitation wavelength;
to collate data in relation to a plurality of fluorescence emission spectra, each fluorescence spectrum generated by the protein sample at a different excitation wavelength to the first excitation wavelength;
generate a non-linear relationship between excitation wavelength and indication characteristic of fluorescence response of the protein sample, the non-linear relationship comprising an indication of at least one characteristic of the conformational state of the protein sample, based upon correlation of the excitation wavelengths and associated evaluated indications characteristic of the fluorescence response of the protein sample; and determine a characterisation of the conformational state of the protein sample based on curvature of the generated non-linear relationship.

* * * * *